United States Patent
Malinowski et al.

(10) Patent No.: US 9,084,380 B2
(45) Date of Patent: *Jul. 14, 2015

(54) SYSTEMS AND METHODS FOR MAKING AND USING ELECTRICAL STIMULATION SYSTEMS WITH IMPROVED RF COMPATIBILITY

(71) Applicant: BOSTON SCIENTIFIC NEUROMODULATION CORPORATION, Valencia, CA (US)

(72) Inventors: Zdzislaw B. Malinowski, Castaic, CA (US); Salomo Murtonen, Pasadena, CA (US); Mizan Rahman, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/525,087

(22) Filed: Oct. 27, 2014

(65) Prior Publication Data

US 2015/0040391 A1  Feb. 12, 2015

Related U.S. Application Data

(63) Continuation of application No. 13/862,205, filed on Apr. 12, 2013, now Pat. No. 8,874,206.

(60) Provisional application No. 61/624,938, filed on Apr. 16, 2012.

(51) Int. Cl.
*A61N 1/36* (2006.01)
*H05K 3/46* (2006.01)
(Continued)

(52) U.S. Cl.
CPC ............... *H05K 3/4685* (2013.01); *A61N 1/36* (2013.01); *A61N 1/36142* (2013.01); *A61N 1/3754* (2013.01); *H01R 13/5224* (2013.01); *H01R 2201/12* (2013.01)

(58) Field of Classification Search
None
See application file for complete search history.

(56) References Cited

U.S. PATENT DOCUMENTS 6,181,969 B1   1/2001  Gord
6,516,227 B1   2/2003  Meadows et al.
(Continued)

OTHER PUBLICATIONS

International Search Report and Written Opinion for International Patent Application No. PCT/US2013/036605 mailed Aug. 20, 2013.
(Continued)

*Primary Examiner* — Brian T Gedeon
*Assistant Examiner* — Ankit Tejani
(74) *Attorney, Agent, or Firm* — Lowe Graham Jones PLLC; Bruce E. Black

(57) ABSTRACT

A method of forming a control module for an electrical stimulation system, the control module including an electronic subassembly disposed in an inner space of a casing and a feedthrough housing disposed along a portion of the casing, includes: forming an RF-diverting assembly having capacitive elements electrically-coupled to a feedthrough ground; electrically-coupling the capacitive elements to conductive pathways extending along a non-conductive substrate; electrically-coupling the conductive pathways to feedthrough pins extending through the feedthrough housing from a location external to the casing to a location within the inner space of the casing; electrically-coupling the conductive pathways to the electronic subassembly such that the conductive pathways electrically-couple the feedthrough pins to the electronic subassembly; electrically-coupling the feedthrough ground to an electrically-conductive portion of the feedthrough housing; and electrically-coupling the electrically-conductive portion of the feedthrough housing to an electrically-conductive portion of an outer surface of the casing.

19 Claims, 16 Drawing Sheets

(51) Int. Cl.
*A61N 1/375* (2006.01)
*H01R 13/52* (2006.01)

(56) References Cited

U.S. PATENT DOCUMENTS

| | | |
|---|---|---|
| 6,609,029 B1 | 8/2003 | Mann et al. |
| 6,609,032 B1 | 8/2003 | Woods et al. |
| 6,741,892 B1 | 5/2004 | Meadows et al. |
| 7,244,150 B1 | 7/2007 | Brase et al. |
| 7,437,193 B2 | 10/2008 | Parramon et al. |
| 7,672,734 B2 | 3/2010 | Anderson et al. |
| 7,761,165 B1 | 7/2010 | He et al. |
| 7,949,395 B2 | 5/2011 | Kuzma |
| 7,974,706 B2 | 7/2011 | Moffitt et al. |
| 8,175,710 B2 | 5/2012 | He |
| 8,224,450 B2 | 7/2012 | Brase |
| 8,364,278 B2 | 1/2013 | Pianca et al. |
| 2002/0166618 A1 | 11/2002 | Wolf et al. |
| 2007/0150036 A1 | 6/2007 | Anderson |
| 2008/0247117 A1 | 10/2008 | Elam et al. |
| 2009/0259265 A1 | 10/2009 | Stevenson et al. |
| 2010/0208397 A1 | 8/2010 | Johnson et al. |
| 2010/0241206 A1 | 9/2010 | Truex et al. |

OTHER PUBLICATIONS

Official Communication for U.S. Appl. No. 13/862,205 mailed Mar. 20, 2014.

SYSTEMS AND METHODS FOR MAKING AND USING ELECTRICAL STIMULATION SYSTEMS WITH IMPROVED RF COMPATIBILITY

CROSS-REFERENCE TO RELATED APPLICATIONS

This application is a continuation of U.S. patent application Ser. No. 13/862,205 filed Apr. 12, 2013 which claims the benefit under 35 U.S.C. §119(e) of U.S. Provisional Patent Application Ser. No. 61/624,938 filed on Apr. 16, 2012, both of which are incorporated herein by reference.

FIELD

The present invention is directed to the area of implantable electrical stimulation systems and methods of making and using the systems. The present invention is also directed to implantable electrical stimulation control modules that modulate undesired propagation of current into electronic systems within the control modules, as well as methods of making and using the control modules and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat incontinence, as well as a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

Conventional implanted electrical stimulation systems are often incompatible with magnetic resonance imaging ("MRI") due to the large radio frequency ("RF") pulses used during MRI. The RF pulses can generate transient signals in the conductors and electrodes of an implanted lead. These signals can have deleterious effects including, for example, unwanted heating of the tissue causing tissue damage, induced currents in the lead, or premature failure of electronic components.

BRIEF SUMMARY

In one embodiment, a method of forming a control module for an electrical stimulation system, the control module including an electronic subassembly disposed in an inner space of a casing and a feedthrough housing disposed along a portion of the casing, includes: forming an RF-diverting assembly, the RF-diverting assembly comprising a plurality of capacitive elements electrically coupled to a feedthrough ground; electrically coupling the plurality of capacitive elements to a plurality of conductive pathways extending along a non-conductive substrate; electrically coupling the plurality of conductive pathways to a plurality of feedthrough pins extending through the feedthrough housing from a location external to the casing to a location within the inner space of the casing; electrically coupling the plurality of conductive pathways to the electronic subassembly such that the plurality of conductive pathways electrically couple the plurality of feedthrough pins to the electronic subassembly; electrically coupling the feedthrough ground to at least one electrically-conductive portion of the feedthrough housing; and electrically coupling the at least one electrically-conductive portion of the feedthrough housing to at least one electrically-conductive portion of an outer surface of the casing.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation control modules that modulate undesired propagation of current into electronic systems within the control modules, as well as methods of making and using the control modules and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, deep brain stimulation leads, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,672,734; 7,761,165; 7,949,395; 7,974,706; 8,175,710; 8,224,450; and 8,364,278; and U.S. Patent Application Publication No. 2007/0150036, all of which are incorporated by reference.

Figure 1:
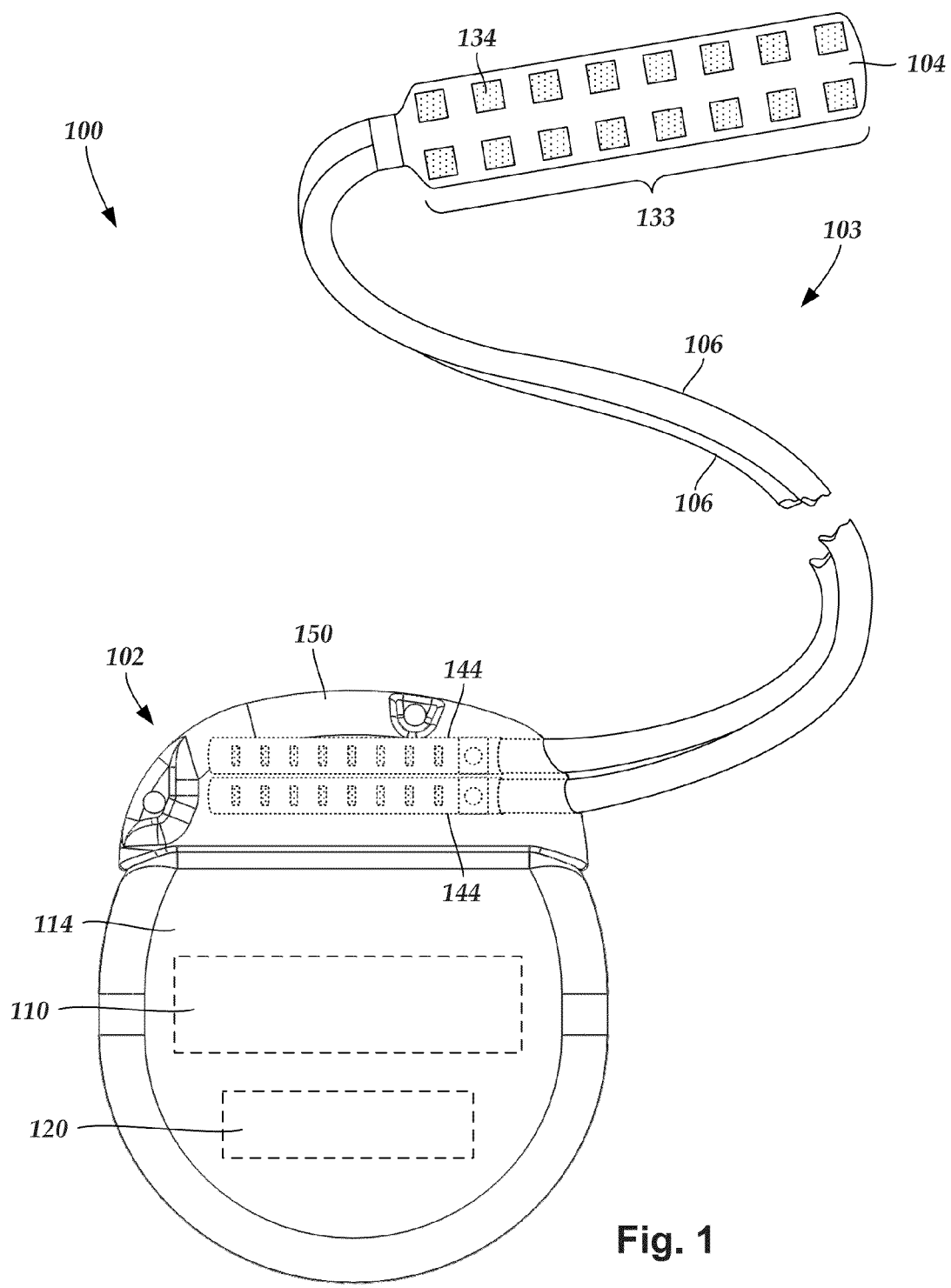
FIG. 1 is a schematic view of one embodiment of an electrical stimulation system that includes a paddle body coupled to a control module via lead bodies, according to the invention.

FIG. 1 illustrates schematically one embodiment of an electrical stimulation system 100. The electrical stimulation system includes a control module (e.g., a stimulator or pulse generator) 102 and a lead 103. The lead 103 including a paddle body 104 and one or more lead bodies 106 coupling the control module 102 to the paddle body 104. The paddle body 104 and the one or more lead bodies 106 form the lead 103. The paddle body 104 typically includes a plurality of electrodes 134 that form an array of electrodes 133. The control module 102 typically includes an electronic subassembly 110 and an optional power source 120 disposed in a sealed housing 114. In FIG. 1, two lead bodies 106 are shown coupled to the control module 102.

The control module 102 typically includes one or more connector assemblies 144 into which the proximal end of the one or more lead bodies 106 can be plugged to make an electrical connection via connector contacts (e.g., 316 in FIG. 3A) disposed in the connector assembly 144 and terminals (e.g., 310 in FIG. 3A) on each of the one or more lead bodies 106. The connector contacts are coupled to the electronic subassembly 110 and the terminals are coupled to the electrodes 134. In FIG. 1, two connector assemblies 144 are shown.

The one or more connector assemblies 144 may be disposed in a header 150. The header 150 provides a protective covering over the one or more connector assemblies 144. The header 150 may be formed using any suitable process including, for example, casting, molding (including injection molding), and the like. In addition, one or more lead extensions 324 (see FIG. 3C) can be disposed between the one or more lead bodies 106 and the control module 102 to extend the distance between the one or more lead bodies 106 and the control module 102.

Figure 2:
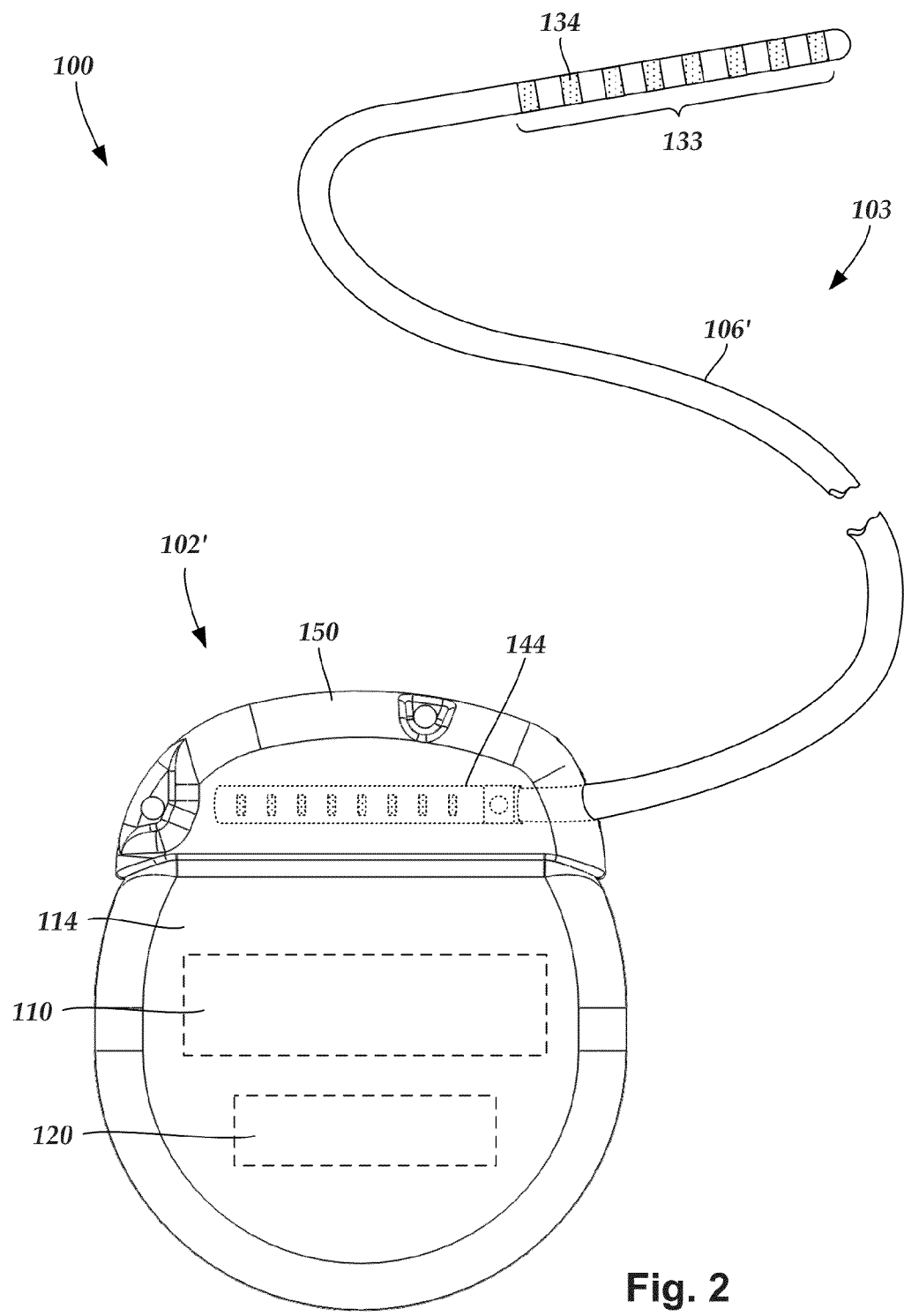
FIG. 2 is a schematic view of another embodiment of an electrical stimulation system that includes a percutaneous lead body coupled to a control module via a lead body, according to the invention.

It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of a lead body 106' forming a percutaneous lead 103, as illustrated in FIG. 2. The percutaneous lead may be isodiametric along the length of the lead body 106''. The lead body 106' can be coupled with a control module 102' with a single connector assembly 144.

The electrical stimulation system or components of the electrical stimulation system, including one or more of the lead bodies 106, the control module 102, and, in the case of a paddle lead, the paddle body 104, are typically implanted into the body of a patient. The electrical stimulation system can be used for a variety of applications including, but not limited to, spinal cord stimulation, brain stimulation, neural stimulation, muscle activation via stimulation of nerves innervating muscle, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, titanium, or rhenium.

The number of electrodes 134 in the array of electrodes 133 may vary. For example, there can be two, three, four, five, six, seven, eight, nine, ten, eleven, twelve, thirteen, fourteen, fifteen, sixteen, or more electrodes 134. As will be recognized, other numbers of electrodes 134 may also be used. In FIG. 1, sixteen electrodes 134 are shown. The electrodes 134 can be formed in any suitable shape including, for example, round, oval, triangular, rectangular, pentagonal, hexagonal, heptagonal, octagonal, or the like.

The electrodes of the paddle body 104 or one or more lead bodies 106 are typically disposed in, or separated by, a non-conductive, biocompatible material including, for example, silicone, polyurethane, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead 103 to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A) are typically disposed at the proximal end of the one or more lead bodies 106 for connection to corresponding conductive contacts (e.g., 316 in FIG. 3A) in connector assemblies (e.g., 144 in FIG. 1) disposed on, for example, the control module 102 (or to other devices, such as conductive contacts on a lead extension, an operating room cable, a splitter, an adaptor, or the like).

Conductive wires (not shown) extend from the terminals (e.g., 310 in FIG. 3A) to the electrodes 134. Typically, one or more electrodes 134 are electrically coupled to a terminal (e.g., 310 in FIG. 3A). In some embodiments, each terminal (e.g., 310 in FIG. 3A) is only coupled to one electrode 134.

The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. The one or more lumens may, optionally, be flushed continually, or on a regular basis, with saline, epidural fluid, or the like. The one or more lumens can be permanently or removably sealable at the distal end.

As discussed above, the one or more lead bodies 106 may be coupled to the one or more connector assemblies 144 disposed on the control module 102. The control module 102 can include any suitable number of connector assemblies 144 including, for example, two three, four, five, six, seven, eight, or more connector assemblies 144. It will be understood that other numbers of connector assemblies 144 may be used instead. In FIG. 1, each of the two lead bodies 106 includes eight terminals that are shown coupled with eight conductive contacts disposed in a different one of two different connector assemblies 144.

Figure 3A:
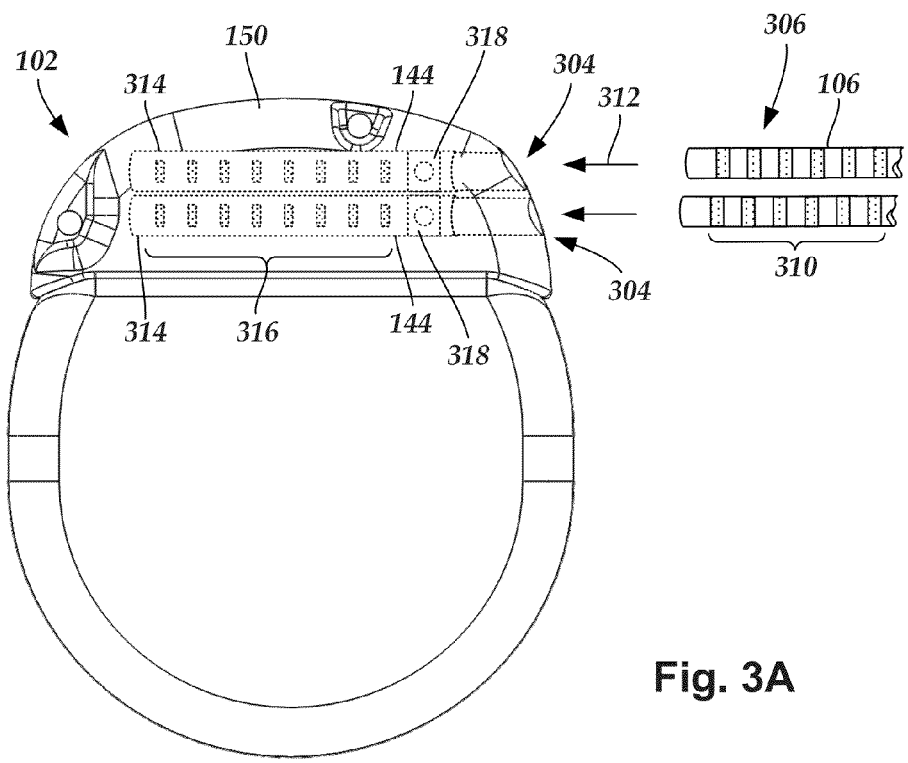
FIG. 3A is a schematic view of one embodiment of a plurality of connector assemblies disposed in the control module of FIG. 1, the connector assemblies configured and arranged to receive the proximal portions of the lead bodies of FIG. 1, according to the invention.
Figure 3B:
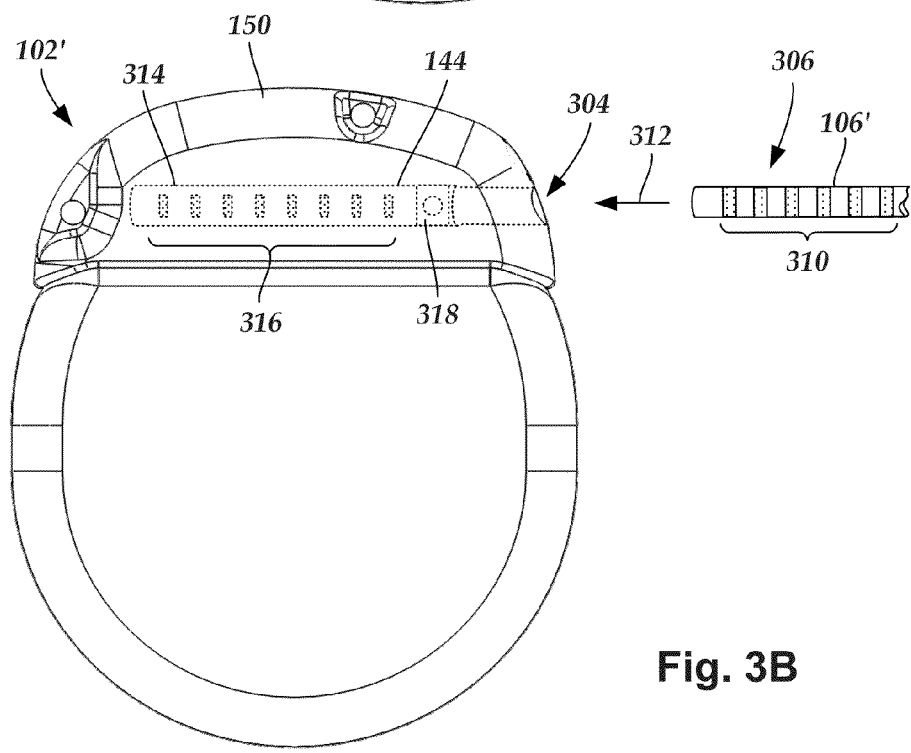
FIG. 3B is a schematic view of one embodiment of a connector assembly disposed in the control module of FIG. 2, the connector assembly configured and arranged to receive the proximal portion of one of the lead body of FIG. 2, according to the invention.

FIG. 3A is a schematic side view of one embodiment of a plurality of connector assemblies 144 disposed on the control module 102. In at least some embodiments, the control module 102 includes two connector assemblies 144. In at least some embodiments, the control module 102 includes four connector assemblies 144. In FIG. 3A, proximal ends 306 of the plurality of lead bodies 106 are shown configured and arranged for insertion to the control module 102. FIG. 3B is a schematic side view of one embodiment of a single connector assembly 144 disposed on the control module 102'. In FIG. 3B, the proximal end 306 of the single lead body 106' is shown configured and arranged for insertion to the control module 102'.

In FIGS. 3A and 3B, the one or more connector assemblies 144 are disposed in the header 150. In at least some embodiments, the header 150 defines one or more ports 304 into which the proximal end(s) 306 of the one or more lead bodies 106/106' with terminals 310 can be inserted, as shown by directional arrows 312, in order to gain access to the connector contacts disposed in the one or more connector assemblies 144.

The one or more connector assemblies 144 each include a connector housing 314 and a plurality of connector contacts 316 disposed therein. Typically, the connector housing 314 defines a port (not shown) that provides access to the plurality of connector contacts 316. In at least some embodiments, one or more of the connector assemblies 144 further includes a retaining element 318 configured and arranged to fasten the corresponding lead body 106/106' to the connector assembly 144 when the lead body 106/106' is inserted into the connector assembly 144 to prevent undesired detachment of the lead body 106/106' from the connector assembly 144. For example, the retaining element 318 may include an aperture through which a fastener (e.g., a set screw, pin, or the like) may be inserted and secured against an inserted lead body 106/106'.

When the one or more lead bodies 106/106' are inserted into the one or more ports 304, the connector contacts 316 can be aligned with the terminals 310 disposed on the one or more lead bodies 106/106' to electrically couple the control module 102 to the electrodes (134 of FIG. 1) disposed at a distal end of the one or more lead bodies 106. Examples of connector assemblies in control modules are found in, for example, U.S. Pat. Nos. 7,244,150 and 8,224,450, which are incorporated by reference.

Figure 3C:
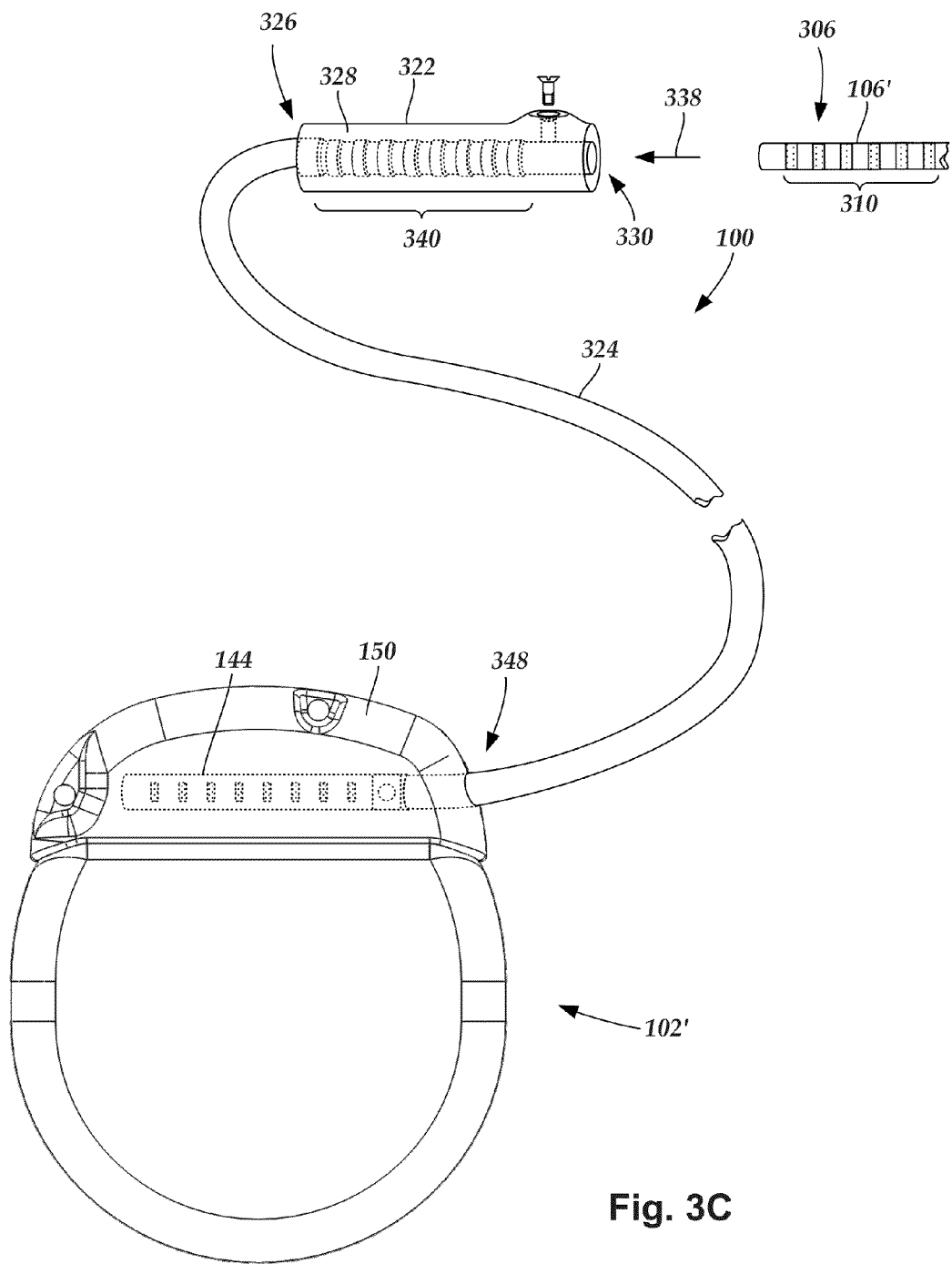
FIG. 3C is a schematic view of one embodiment of a proximal portion of the lead body of FIG. 2, a lead extension, and the control module of FIG. 2, the lead extension configured and arranged to couple the lead body to the control module, according to the invention.

In at least some embodiments, the electrical stimulation system includes one or more lead extensions. The one or more lead bodies 106/106' can be coupled to one or more lead extensions which, in turn, are coupled to the control module 102/102'. In FIG. 3C, a lead extension connector assembly 322 is disposed on a lead extension 324. The lead extension connector assembly 322 is shown disposed at a distal end 326 of the lead extension 324. The lead extension connector assembly 322 includes a contact housing 328. The contact housing 328 defines at least one port 330 into which a proximal end 306 of the lead body 106' with terminals 310 can be inserted, as shown by directional arrow 338. The lead extension connector assembly 322 also includes a plurality of connector contacts 340. When the lead body 106' is inserted into the port 330, the connector contacts 340 disposed in the contact housing 328 can be aligned with the terminals 310 on the lead body 106 to electrically couple the lead extension 324 to the electrodes (134 of FIG. 1) disposed at a distal end (not shown) of the lead body 106'.

The proximal end of a lead extension can be similarly configured and arranged as a proximal end of a lead body. The lead extension 324 may include a plurality of conductive wires (not shown) that electrically couple the connector contacts 340 to terminal on a proximal end 348 of the lead extension 324. The conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a lead extension connector assembly disposed in another lead extension. In other embodiments (as shown in FIG. 3C), the proximal end 348 of the lead extension 324 is configured and arranged for insertion into the connector assembly 144 disposed on the control module 102'.

It will be understood that the control modules 102/102' can receive either lead bodies 106/106' or lead extensions 324. It will also be understood that the electrical stimulation system 100 can include a plurality of lead extensions 224. For example, each of the lead bodies 106 shown in FIGS. 1 and 3A can, alternatively, be coupled to a different lead extension 224 which, in turn, are each coupled to different ports of a two-port control module, such as the control module 102 of FIGS. 1 and 3A.

Figure 4A:
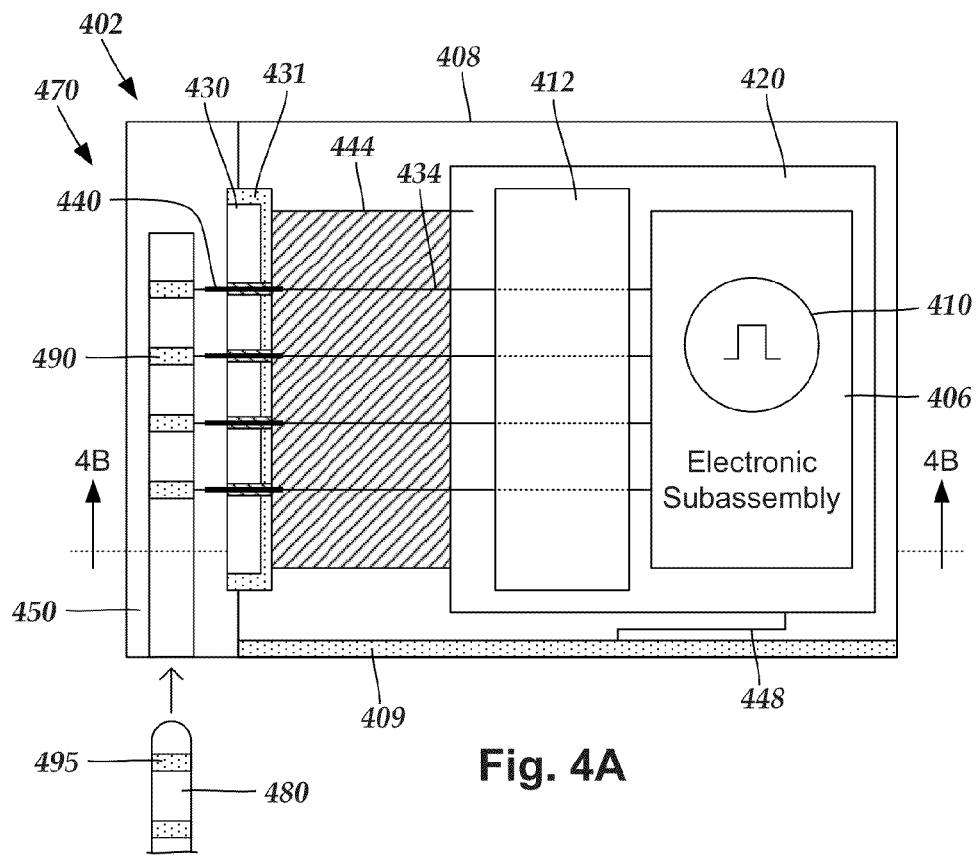
FIG. 4A is a schematic view of one embodiment of a portion of a control module suitable for providing electrical signals to an electrical stimulation lead, the control module including an electronic subassembly disposed in a casing and a feedthrough housing enabling current to propagate into the casing, according to the invention.
Figure 4B:
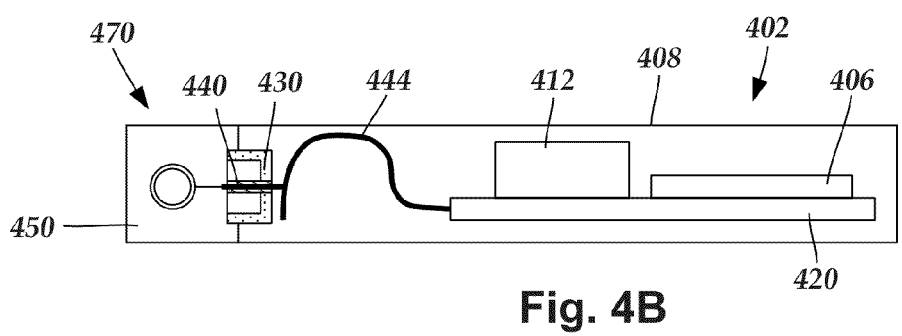
FIG. 4B is a schematic side view of one embodiment of a portion of the control module of FIG. 4A, according to the invention.

FIG. 4A is a schematic view of one embodiment of a portion of a control module 402 suitable for providing electrical signals to an electrical stimulation lead (e.g., lead 103 of FIG. 1 or 2). FIG. 4B is a schematic cross-sectional side view of one embodiment of a portion of the control module 402. The control module 402 includes an electronic subassembly 406 disposed in a sealed control module casing 408. The electronic subassembly 406 includes a pulse generator 410 for providing electrical signals. The electronic subassembly 406 can be mounted on a printed circuit board ("PCB") 420. Optionally, the control module 402 includes a power source 412 (such as a battery) coupled to the electronic subassembly 406.

A feedthrough housing 430 is disposed along a wall of the control module casing 408. A plurality of feedthrough pins, such as feedthrough pin 440, are at least partially disposed in the feedthrough housing 430 and provide conductive paths across the sealed control module casing 408. In at least some embodiments, a connector assembly 470 is disposed on an exterior portion of the control module casing 408. The connector assembly 470 may, optionally, be disposed in a header 450 (See e.g., 150 in each of FIGS. 1-3C). In which case, in at least some embodiments the feedthrough housing 430 is disposed along a portion of the control module casing 408 that abuts the header 450. The connector assembly 470 can be configured and arranged to receive one or more leads 480. Optionally, the connector assembly 430 can be configured and arranged to receive one or more lead extensions (see e.g., 324 in FIG. 3C) in addition to, or in lieu of, one or more leads 480.

In at least some embodiments, the feedthrough pin 440 provide conductive paths across the sealed control module casing 408 between the connector assembly 470 and the electronic subassembly 406. Thus, the feedthrough pins 440 can be used for electrically coupling the electrodes disposed along the lead with the electronic subassembly 406 when the lead 480 (or lead extension) is inserted into the connector assembly 470.

The portions of the feedthrough pins 440 external to the control module casing 408 couple electrically with connector contacts, such as connector contact 490, disposed in the connector assembly 470 which, in turn, are configured and arranged to couple electrically with terminals 495 of the insertable lead 480 (or lead extension).

The portions of the feedthrough pins 440 disposed within the control module casing 408 couple to the electronic subassembly 406 via conductive pathways, such as conductive pathway 434. In at least some embodiments, at least a portion of a length of each of the conductive pathways 434 is formed on a non-conductive substrate, such as a flex circuit 444, or the like. In at least some embodiments, at least a portion of the lengths of the conductive pathways are formed on the PCB 420. In at least some embodiments, at least a portion of the lengths of the conductive pathways are formed on the flex circuit 444 and the PCB 420. In at least some embodiments, the number of conductive pathways 434 is equal to the number of feedthrough pins 440.

The control module casing 408 is at least partially formed from one or more conductive materials 409 (e.g., one or more metals, alloys, conductive polymers, or the like). In at least some embodiments, the control module casing 408 is entirely formed from one or more conductive materials 409. In at least some alternate embodiments, the control module casing 408 is formed partially from one or more conductive materials and partially from one or more non-conductive materials. When the control module casing 408 is formed partially from one or more conductive materials and partially from one or more non-conductive materials, the conductive and non-conductive materials can be arranged in any suitable configuration. In at least some embodiments, the control module casing 408 is formed from one or more conductive regions (e.g., one or more plates, or the like) surrounded by one or more non-conductive materials.

In at least some embodiments, the conductivity of the conductive portion(s) of the control module casing 408 can be used to ground the electronic subassembly 406. In FIG. 4A, the electronic subassembly 406 is shown grounded to the conductive portion 409 of the control module casing 408 via one or more ground lines 448. At least some of the walls of the feedthrough housing 430 are at least partially formed from one or more conductive materials 431 (e.g., one or more metals, alloys, conductive polymers, or the like). Non-conductive material is disposed along the interior of the feedthrough housing 430 to electrically isolate the feedthrough pins 440 from one another and from the conductive portions of the walls 431 of the feedthrough housing 430.

Conventional electrical stimulation systems may be potentially unsafe for use with magnetic resonance imaging ("MRI") due to the effects of electromagnetic fields in an MRI environment. One mechanism for generating an electrical interaction between the electrical stimulation system and RF irradiation is common-mode coupling of the applied electromagnetic fields. This coupling can be modeled as a series of distributed sources along an elongated conductive structure, such as a lead, or conductors within a lead. Common-mode induced RF currents can reach amplitudes of greater than one ampere in MRI environments. Such currents can cause heating and potentially damaging conditions within electronic circuits.

Some of the deleterious effects of RF irradiation may include, for example, inducing current in the lead, causing undesired heating of the lead that may potentially cause tissue damage, undesired or unexpected operation of electronic components, or premature failure of electronic components. Additionally, when an electrical stimulation system is used within an MRI scanner environment, the electrical interactions between the electrical stimulation system and the MRI may cause distortions in images formed by the MRI system.

When the lead (or lead extension) is inserted into the connector assembly, and when the electrical stimulation system is implanted into a patient and exposed to RF irradiation (e.g., during an MRI procedure), undesired induced currents can propagate along the lead and along the conductive pathways of the control module to the electronic subassembly.

Figure 5A:
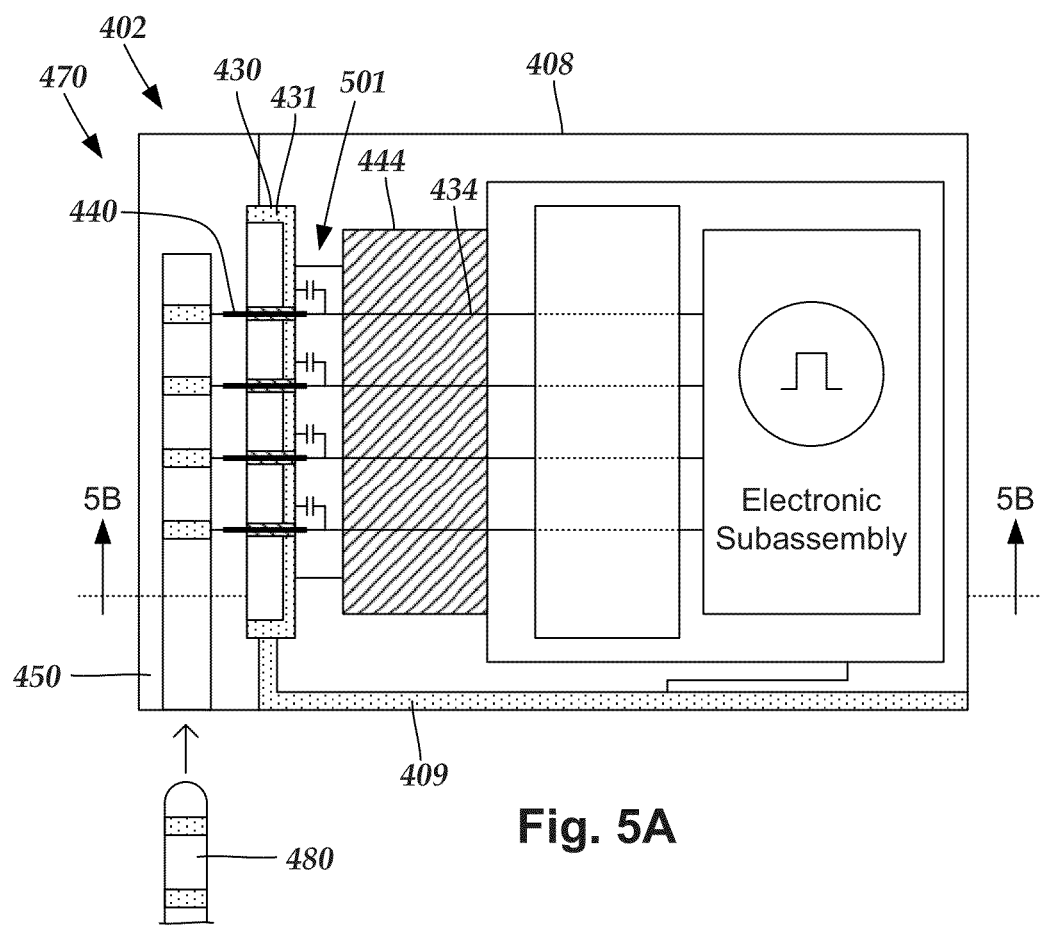
FIG. 5A is a schematic view of another embodiment of the control module of FIG. 4A, the control module including a RF-diverting assembly disposed in the feedthrough housing of the control module, according to the invention.

Turning to FIG. 5A, as herein described an RF-diverting assembly is disposed in the control module to filter out RF-induced currents propagating into the control module from the lead when the lead is received by the control module (see e.g., FIGS. 1 and 2). The RF-diverting assembly diverts the undesired RF-induced current before the RF-induced current reaches the electronic subassembly, thereby reducing, or even preventing, damage to the system electronics caused by exposure to RF irradiation. In at least some embodiments, the RF-diverting assembly diverts the undesired RF-induced current while providing little, if any, interference with the propagation of operational electrical signals between the electrodes and the electrical subassembly.

Figure 5B:
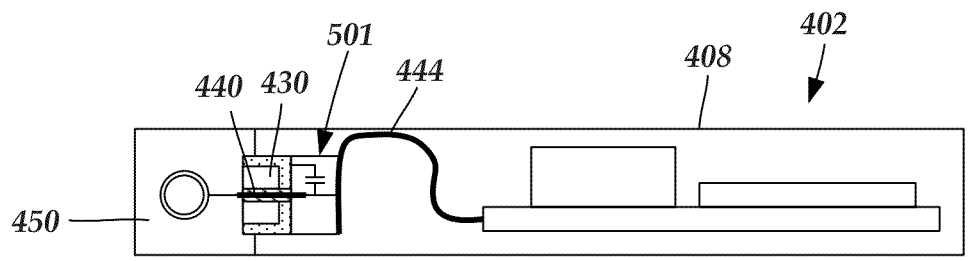
FIG. 5B is a schematic cross-sectional side view of one embodiment of the RF-diverting assembly of FIG. 5A disposed in the control module of FIG. 4A, according to the invention.

FIG. 5A is a schematic top view of one embodiment of a RF-diverting assembly 501 disposed in the control module 402. FIG. 5B is a schematic cross-sectional side view of one embodiment of the RF-diverting assembly 501 disposed in the control module 402. In at least some embodiments, the RF-diverting assembly 501 is configured and arranged to shunt most, if not all, of the undesired induced current to the conductive portion 431 of the feedthrough housing 430 which, in turn, shunts the induced current to the conductive portion 409 of the control module casing 408.

In at least some embodiments, the RF-diverting assembly 501 is also configured and arranged to enable most, if not all, of the operational current to propagate along the feedthrough pins 440, between the connector assembly 470 and the electronic subassembly 406, without being diverted. In at least some embodiments, the RF-diverting assembly 501 is coupled to each of the feedthrough pins 440. In at least some embodiments, the RF-diverting assembly 501 is coupled to each of the conductive pathways 434. In at least some embodiments, the RF-diverting assembly 501 is coupled to each of the feedthrough pins 440 and to each of the conductive pathways 434. In at least some embodiments, the RF-diverting assembly 501 is coupled to the flex circuit 444. In at least some embodiments, the RF-diverting assembly 501 is coupled to the feedthrough housing 430.

The control module 402 shown in FIGS. 4A-5B is configured to receive current along up to four feedthrough pins. Consequently, the RF-diverting assembly 501 shown in FIGS. 5A-5B is configured and arranged to disperse induced current propagating along up to four feedthrough pins. The control module 402 can be configured to receive leads (or lead extensions) with any suitable number of terminals/electrodes for providing efficacious stimulation to a patient including, for example, one, two, three, four, five, six, seven, eight, nine, ten, eleven, twelve, fourteen, sixteen, eighteen, twenty, twenty-four, twenty-eight, thirty-two, or more terminals/electrodes. It will be understood that the RF-diverting assembly 501 can be adapted, as desired, to disperse current propagating along each of the feedthrough pins, regardless of the number of feedthrough pins.

Figure 6A:
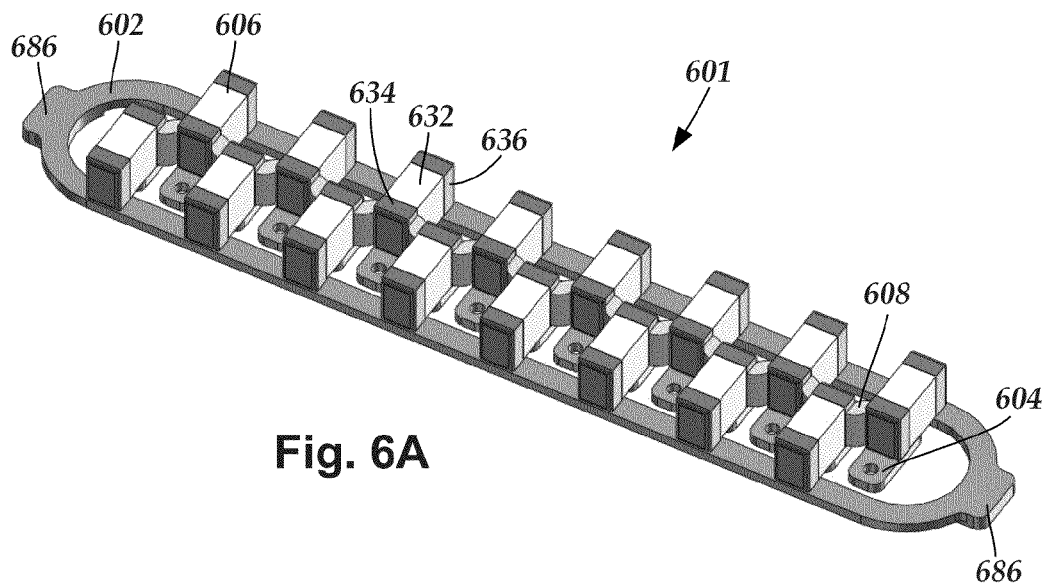
FIG. 6A is a schematic top perspective view of one embodiment of a RF-diverting assembly, the RF-diverting assembly including a feedthrough ground, a plurality of conductive pads, and a plurality of capacitive elements, according to the invention.
Figure 6B:
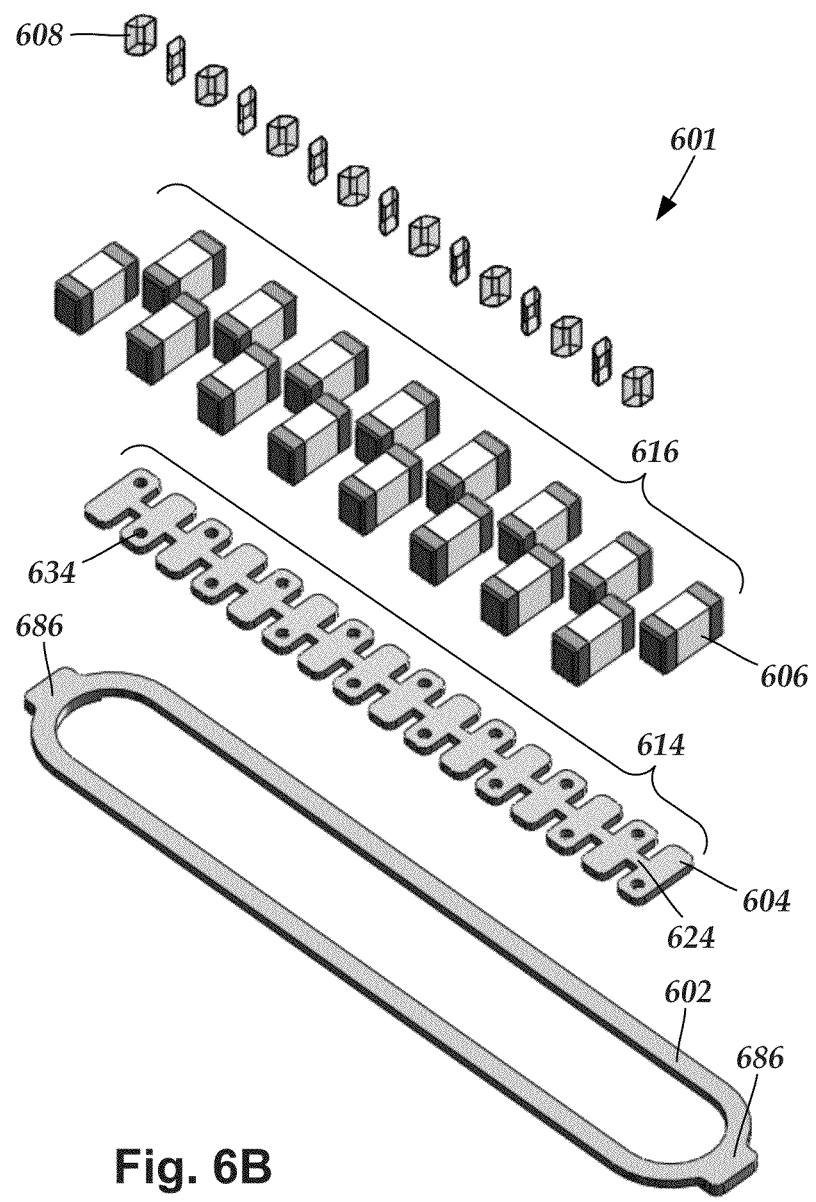
FIG. 6B is a schematic top perspective exploded view of one embodiment of the RF-diverting assembly of FIG. 6A, according to the invention.

FIG. 6A is a schematic top perspective view of one embodiment of the RF-diverting assembly 601. FIG. 6B is a schematic top perspective exploded view of one embodiment of the RF-diverting assembly 601. The RF-diverting assembly 601 includes a feedthrough ground 602; a plurality of conductive pads, such as conductive pad 604, arranged into an array 614 of conductive pads; and a plurality of capacitive elements, such as capacitive element 606, arranged into an array 616 of conductive pads.

In at least some embodiments, the conductor pads 604 are electrically coupled to at least one of the feedthrough pins 440 or the conductive pathways 434. The capacitive elements 606 extend between the conductor pads 606 and the feedthrough ground 602 and provide a relatively-low resistance path for undesired current to propagate along. The feedthrough ground 602 is electrically coupled to the conductive portion 431 of the feedthrough housing 430 which, in turn, is electrically coupled to the conductive portion 409 of the control module casing 408.

Any suitable capacitive element 606 may be used. In FIG. 6A (and in other figures), the capacitive elements 606 are shown with a dielectric 632 disposed between a first plate 634 and a second plate 636. In at least some embodiments, the capacitive element 606 can be disposed on the RF-diverting assembly 601 such that each of the first plates 634 is coupled to a different one of the conductor pads 604 and each of the second plates 636 is coupled to the feedthrough ground 602.

The capacitive elements 606 can have any capacitance suitable for providing a low impedance path for induced currents, while providing a high impedance path for operational currents. During a typical MRI procedure, a patient may be exposed to frequencies (e.g., approximately 64 MHz to 128 MHz) that are much higher than the operational frequencies of the electronic stimulation system. Accordingly, in at least some embodiments the capacitive elements 606 are configured and arranged to filter out frequencies above (or below) the operational frequencies of the electrical stimulation system.

In at least some embodiments, the capacitance of each of the capacitive elements 606 is no greater than 2000 pF. In at least some embodiments, the capacitance of each of the capacitive elements 606 is no less than 1000 pF. In at least some embodiments, the capacitance of each of the capacitive elements 606 is in a range that is no greater than 2000 pF and is no less than 1000 pF.

Optionally, adhesive 608 may be applied to the current-dispensing apparatus 601 to provide mechanical support for the RF-diverting assembly 601. For example, in at least some embodiments, adhesive 608 is disposed between adjacent capacitive elements 606 to provide additional mechanical support between the adjacent capacitive elements 606. In at least some embodiments, the adhesive 608 is disposed between adjacent first plates 634 of the capacitive elements 606.

The RF-diverting assembly 601 can be adapted to shunt current propagating along any suitable number of feedthrough pins. In FIGS. 6A-6B (and in other figures), the RF-diverting assembly 601 is configured to shunt current propagating along up to sixteen feedthrough pins. The RF-diverting assembly 601 can include any suitable number of capacitive elements. The number of capacitive elements disposed on the RF-diverting assembly 601 can be fewer than, equal to, or greater than the number of feedthrough pins of the control module 402. The RF-diverting assembly 601 can include any suitable number of conductive pads. The number of conductive pads disposed on the RF-diverting assembly 601 can be fewer than, equal to, or greater than the number of feedthrough pins of the control module 402.

Optionally, the feedthrough ground 602 includes one or more coupling pads 686 for facilitating coupling of the feedthrough ground 602 to the one or more conductive portions 431 of the feedthrough housing 430. In FIGS. 6A-6B (and in other figures), the one or more coupling pads 686 are disposed along opposing ends of the feedthrough housing 430.

In at least some embodiments, the feedthrough ground 602 is also configured and arranged to mechanically couple to the flex circuit 444. The feedthrough ground 602 can be formed from any non-magnetic, conductive material suitable for coupling to both the feedthrough housing 430 and the flex circuit 444. In at least some embodiments, the conductive portion 431 of the feedthrough housing 430 is formed from titanium. In which case, it may be advantageous to form the feedthrough ground 502 from at least one of nickel or nickel alloy so that the feedthrough ground 602 can be coupled (e.g., resistant welded, laser welded, or the like) directly to the conductive portion 431 of the feedthrough housing 430. It may also be advantageous to form the feedthrough ground 602 from nickel so that the feedthrough ground 602 can be coupled (e.g., soldered, adhesively coupled with a conductive adhesive, or the like) directly to the flex circuit 444.

The feedthrough ground 602 can be formed in any shape suitable for receiving current from each of the capacitive elements 606 and enabling propagation of that current to the feedthrough housing 430. In at least some embodiments, the feedthrough ground 602 is formed as a closed loop. In at least some embodiments, the feedthrough ground 602 is formed as an elongated closed loop. In at least some embodiments, the feedthrough ground 602 is formed as a closed loop configured and arranged to receive the plurality of capacitive elements 606.

In at least some embodiments, at least some of the plurality of conductive pads 604 are coupled to one another via connecting links 624 prior to insertion of the RF-diverting assembly 601. In at least some embodiments, prior to insertion of the RF-diverting assembly 601 each of the plurality of conductive pads is coupled to one another such that each of the conductive pads 604 form a single unit. In at least some embodiments, each of the plurality of conductive pads 604 defines an aperture 634. In at least some embodiments, at least some of the conductive pads 604 are arranged in the same configuration as the feedthrough pins 440 of the control module 402.

Figure 7A:
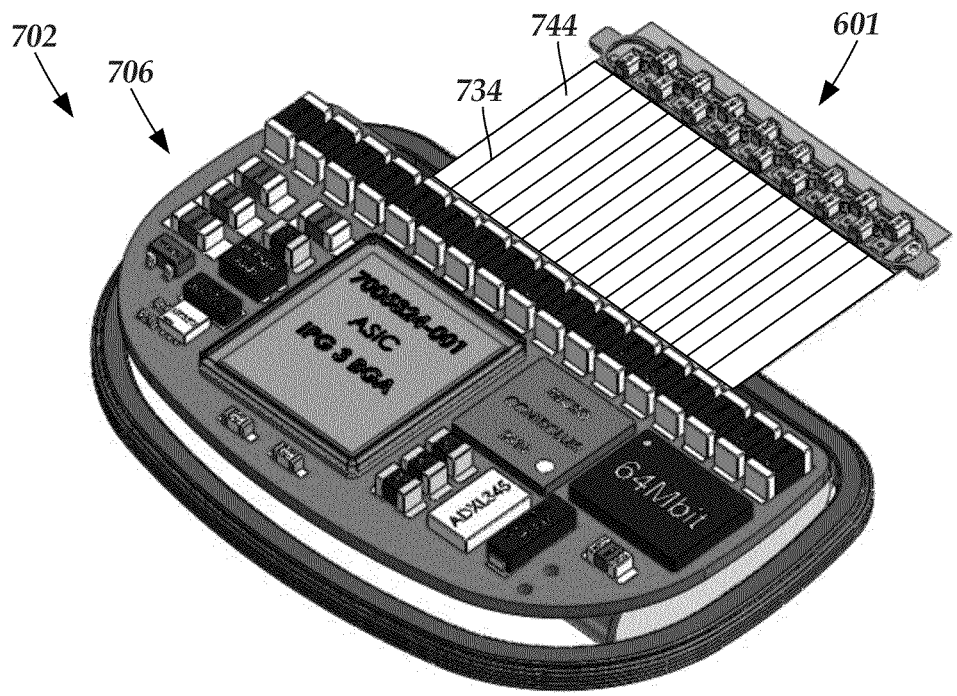
FIG. 7A is a schematic top perspective view of one embodiment of the RF-diverting assembly of FIG. 6A disposed in a control module, where the RF-diverting assembly is coupled to a flex circuit disposed in the control module, according to the invention.
Figure 7B:
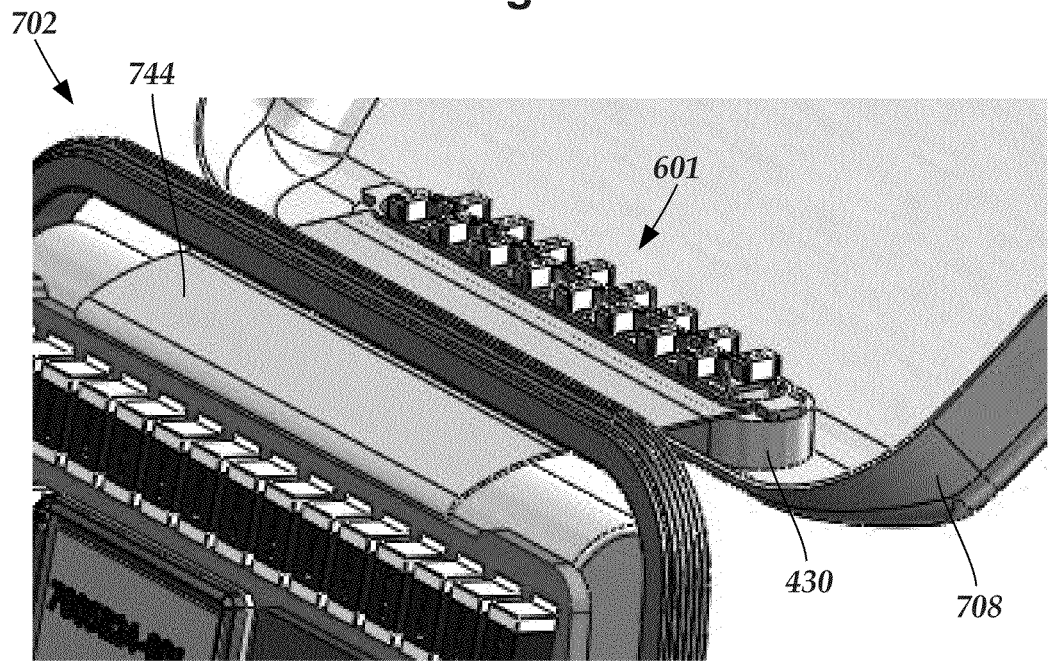
FIG. 7B is a schematic top perspective view of one embodiment of the RF-diverting assembly of FIG. 6A disposed in the control module of FIG. 7A, where the RF-diverting assembly is coupled to the flex circuit of FIG. 7A and also to a feedthrough housing disposed in the control module, according to the invention.

FIG. 7A is a schematic top perspective view of one embodiment of a control module 702 with a portion of the casing (see e.g., 408 in FIGS. 4A-5B) removed. The control module 702 includes a flex circuit 744. The RF-diverting assembly 601 is disposed on the flex circuit 744. Conductive pathways 734 disposed on the flex circuit 744 electrically couple the RF-diverting assembly 601 to the electronic sub-assembly 706. FIG. 7B is a schematic top perspective view of one embodiment of a portion of the control module 702. The control module 702 includes a partially-opened casing 708 and a feedthrough housing 730 disposed on an inner surface of the casing 708.

The RF-diverting assembly 601 is coupled to the flex circuit 744 and also to the feedthrough housing 730. In FIG. 7B, the RF-diverting assembly 601 is coupled to the feedthrough housing 430 such that the flex circuit 744 is sandwiched between the RF-diverting assembly 601 and the feedthrough housing 430.

Figure 8A:
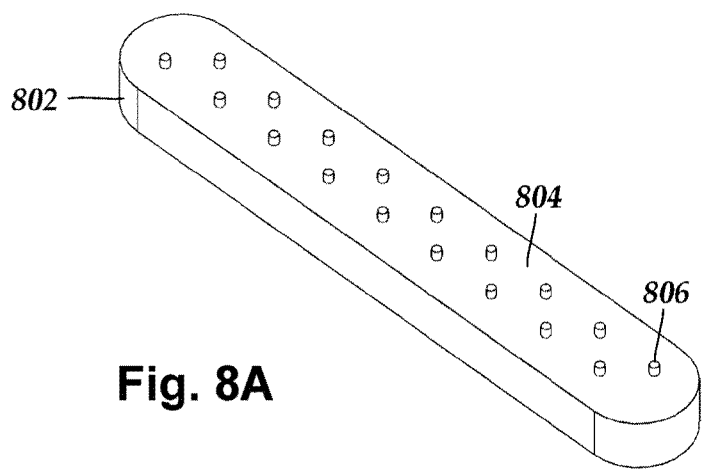
FIG. 8A is a schematic top perspective view of one embodiment of a base suitable for facilitating fabrication of the RF-diverting assembly of FIG. 6A, according to the invention.

The RF-diverting assembly 601 can be formed in any suitable manner. FIGS. 8A-8E illustrate one of many possible ways to form the RF-diverting assembly 601. FIG. 8A is a schematic top perspective view of one embodiment of a base 802 suitable for facilitating fabrication of the RF-diverting assembly 601. In at least some embodiments, the base 802 is configured to provide consistent spacing between components of the RF-diverting assembly 601 prior to coupling the components together.

The base 802 includes a major surface 804 along which a plurality of pins, such as pin 806, extend. In at least some embodiments, at least some of the pins 806 are arranged along the major surface 804 in the same configuration as the feedthrough pins 440 of the control module 402. The major surface 804 and the pins 806 can be formed from any suitable non-solderable metallic material including, for example, magnesium, chromium, titanium, stainless steel, aluminum, or the like.

Figure 8B:
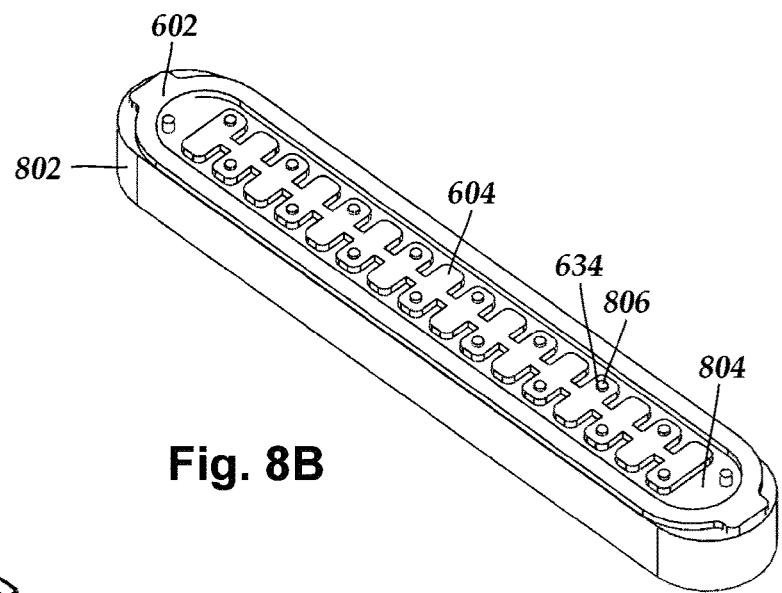
FIG. 8B is a schematic top perspective view of one embodiment of the feedthrough ground of FIG. 6A and the conductive pads of FIG. 6A disposed on the base of FIG. 8A, according to the invention.

FIG. 8B is a schematic top perspective view of one embodiment of the feedthrough ground 602 and the conductive pads 604 disposed on the major surface 804 of the base 802. In FIG. 8B, the pins 806 are spaced along the major surface 804 so that when the feedthrough ground 602 and the conductive pads 604 are disposed on the base 802 the feedthrough ground 602 and the conductive pads 604 are particularly aligned with one another. In at least some embodiments, the conductive pads 604 can be disposed on the base 802 such that the apertures 634 of the conductive pads 604 mate with at least some of the pins 806. In FIG. 8B, the feedthrough ground 602 and the conductive pads 604 are aligned such that the conductive pads 604 are disposed within the feedthrough ground 602.

Figure 8C:
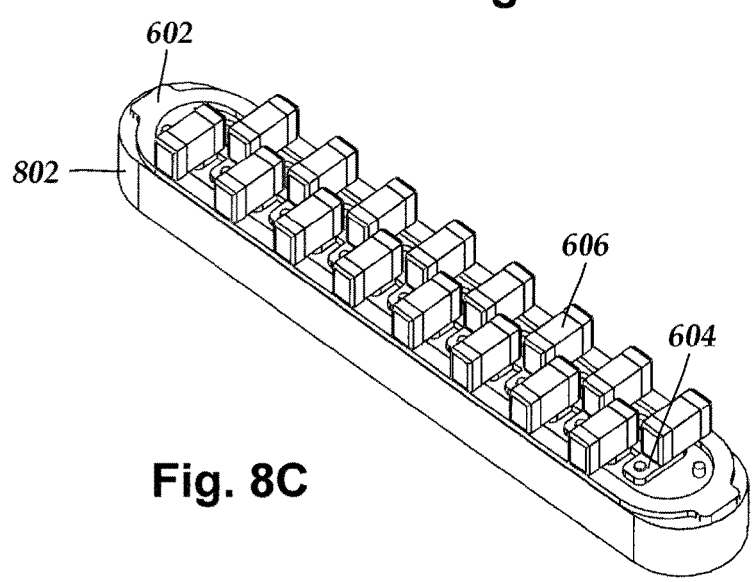
FIG. 8C is a schematic top perspective view of one embodiment of the capacitive elements of FIG. 6A coupled to both the feedthrough ground of FIG. 6A and the conductive pads of FIG. 6A which, in turn, are both disposed on the base of FIG. 8A, according to the invention.

In at least some embodiments, when the feedthrough ground 602 and the conductive pads 604 are aligned (as can be facilitated by the base 802), the capacitive elements can be used to couple each of the conductive pads 604 to the feedthrough ground 602. FIG. 8C is a schematic top perspective view of one embodiment of the capacitive elements 606 disposed on both the feedthrough ground 602 and the conductive pads 604. The capacitive elements 606 can be coupled to the feedthrough ground 602 and the conductive pads 604 in any suitable manner (e.g., soldering, adhesively coupled with conductive adhesive, or the like). In at least some embodiments, adjacent capacitive elements 606 of the plurality of capacitive elements 606 are coupled together via adhesive (608 in FIG. 6B) to provide mechanical reinforcement.

Figure 8D:
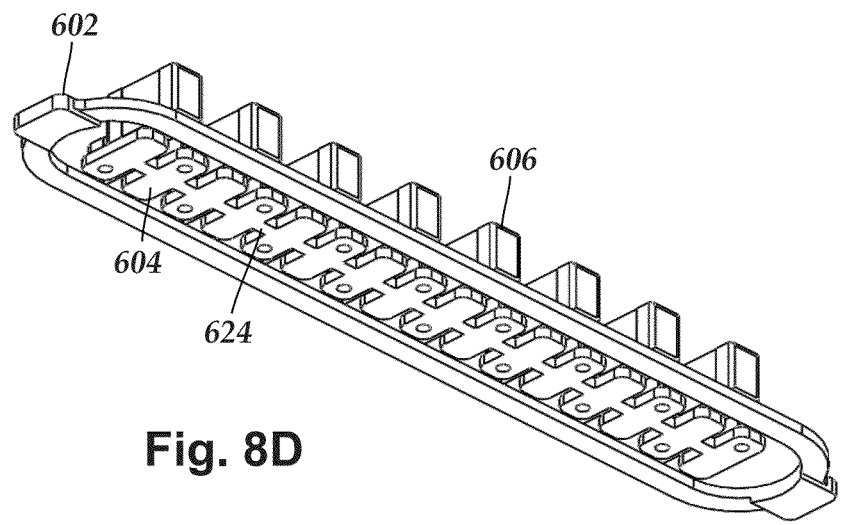
FIG. 8D is schematic bottom perspective view of one embodiment of the feedthrough ground of FIG. 6A, the capacitive elements of FIG. 6A, and the conductive pads of FIG. 6A removed from the base of FIG. 8A, where the plurality of conductive pads are coupled to one another via connecting links, according to the invention.

In at least some embodiments, when the capacitive elements 606 are coupled to the feedthrough ground 602 and the conductive pads 604 and the adhesive is set (if applicable), the capacitive elements 606, conductive pads 604, and feedthrough ground 602 are removed from the base 802. FIG. 8D is schematic bottom perspective view of one embodiment of the capacitive elements 606, conductive pads 604, and feedthrough ground 602. As shown in FIG. 8D, the capacitive elements 606, conductive pads 604, and feedthrough ground 602 have been removed from the base 802. Adjacent conductive pads 604 are connected to one another via the connecting links 624.

Figure 8E:
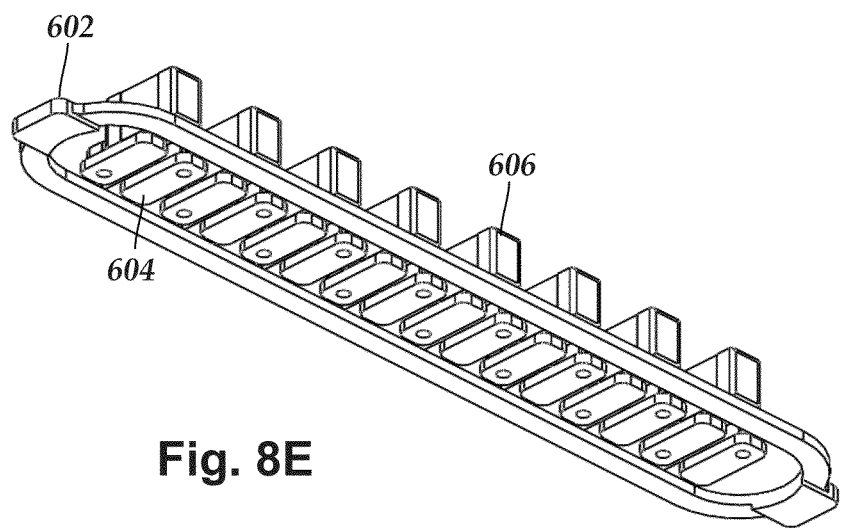
FIG. 8E is schematic bottom perspective view of one embodiment of the feedthrough ground of FIG. 6A, the capacitive elements of FIG. 6A, and the conductive pads of FIG. 6A removed from the base of FIG. 8A, where the plurality of conductive pads are separated from one another along the connecting links of FIG. 8D, according to the invention.

In at least some embodiments, when the capacitive elements 606, conductive pads 604, and feedthrough ground 602 are removed from the base 802, the conductive pads 604 are separated from one another. FIG. 8E is schematic bottom view of one embodiment of the plurality of conductive pads 604 separated from one another by removal of the connecting links 624. The conductive pads 604 can be separated from one another along the connecting links 624 in any suitable manner including, for example, laser cutting.

Figure 9A:
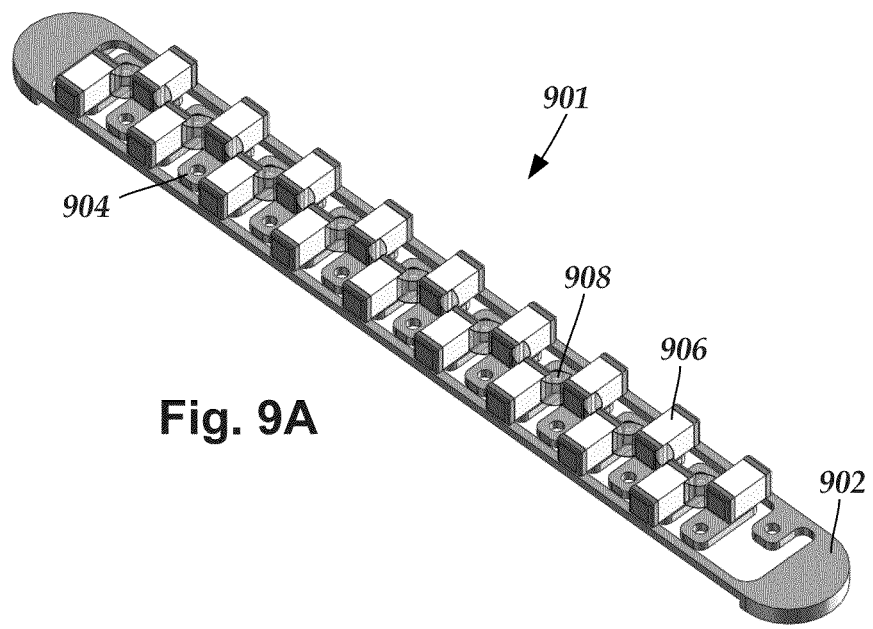
FIG. 9A is a schematic top perspective view of another embodiment of a RF-diverting assembly, the RF-diverting assembly including a feedthrough ground, a plurality of conductive pads coupled to the ground ring, and a plurality of capacitive elements, according to the invention.

Turning to FIG. 9A, in at least some embodiments the conductive pads are coupled to the feedthrough ground prior to assembly of the RF-diverting assembly. In at least some embodiments, prior to assembly of the RF-diverting assembly the conductive pads are coupled to the feedthrough ground in addition to being coupled to one another. In at least some embodiments, prior to assembly of the RF-diverting assembly the conductive pads are coupled to the feedthrough ground in lieu of being coupled to one another.

Figure 9B:
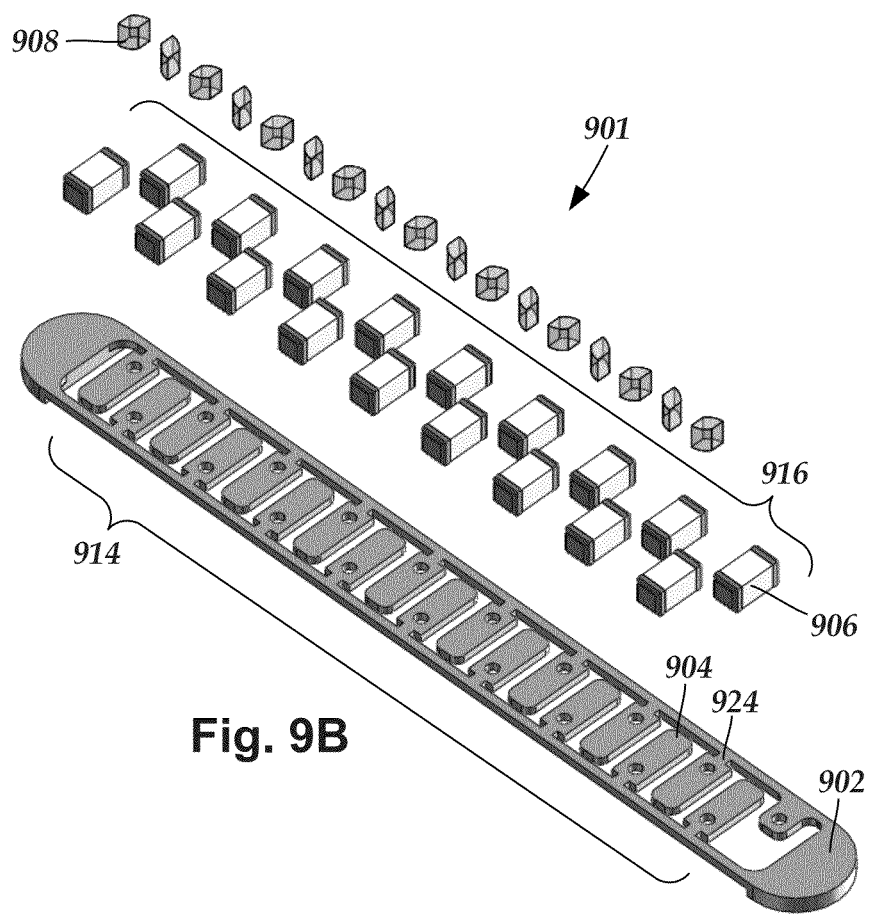
FIG. 9B is a schematic top perspective exploded view of one embodiment of the RF-diverting assembly of FIG. 9A, according to the invention.

FIG. 9A is a schematic top perspective view of another embodiment of a RF-diverting assembly 901. FIG. 9B is a schematic top perspective exploded view of one embodiment of the RF-diverting assembly 901. The RF-diverting assembly 901 includes a feedthrough ground 902; a plurality of conductive pads, such as conductive pad 904, arranged into an array 914 of conductive pads; and a plurality of capacitive elements, such as capacitive element 906, arranged into an array 916 of conductive pads. Optionally, adhesive 908 may be applied to the current-dispending apparatus 901 to provide mechanical support. For example, in at least some embodiments adhesive 908 is disposed between adjacent capacitive elements 906.

As shown in FIG. 9B, the conductive pads 904 are coupled to the feedthrough ground 902 prior to coupling the capacitive elements 906 to the conductive pads 904 and the feedthrough ground 902. In at least some embodiments, the conductive pads 904 are coupled to the feedthrough ground 902 via connecting links, such as connecting link 924. In at least some embodiments, the conductive pads 904 are arranged in the same configuration as the feedthrough pins 440 of the control module 402.

When, as shown in FIG. 9B, the conductive pads 904 are coupled to the feedthrough ground 902 prior to coupling the capacitive elements 906 to the conductive pads 904 and the feedthrough ground 902 a base (see e.g., base 802 in FIG. 8A) may not be needed during the manufacturing process to facilitate alignment of the conductive pads 904 with the feedthrough ground 902.

Figure 9C:
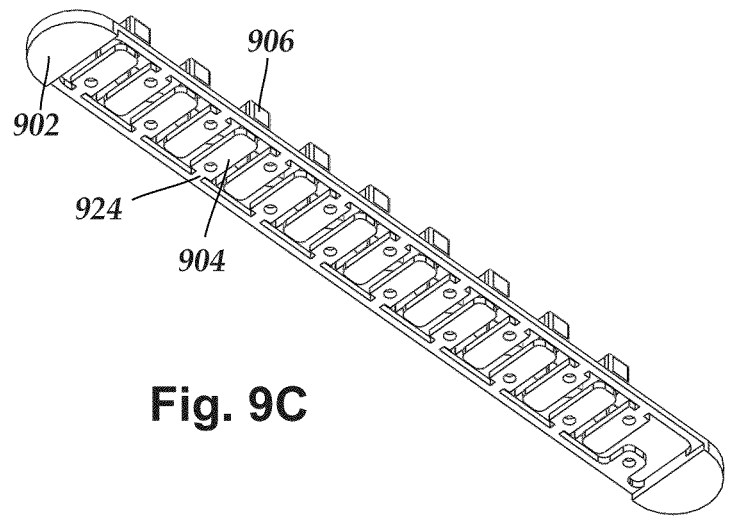
FIG. 9C is schematic bottom perspective view of one embodiment of the feedthrough ground of FIG. 9A, the capacitive elements of FIG. 9A, and the conductive pads of FIG. 9A, where the plurality of conductive pads are coupled to the feedthrough ground via connecting links, according to the invention.
Figure 9D:
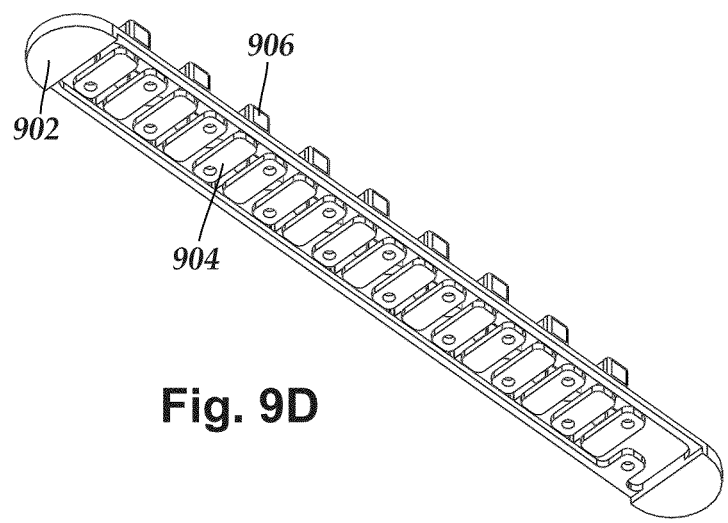
FIG. 9D is schematic bottom perspective view of one embodiment of the feedthrough ground of FIG. 9A, the capacitive elements of FIG. 9A, and the conductive pads of FIG. 9A, where the plurality of conductive pads are separated from the feedthrough ground along the connecting links of FIG. 9C, according to the invention.

FIG. 9C is schematic bottom perspective view of one embodiment of each of the conductive pads 904 coupled to the feedthrough ground 902 via the capacitive elements 906. The conductive pads 904 are also coupled to the feedthrough ground 902 via the connecting links 924. FIG. 9D is schematic bottom perspective view of one embodiment of each of the conductive pads 904 coupled to the feedthrough ground 902 via the capacitive elements 906. The connecting links 924 have been removed to separate the direct connection between the conductive pads 904 and the feedthrough ground 902 so that the conductive pads 904 are only coupled to the feedthrough ground 902 via the capacitive elements 906. The connecting link 924 can be removed using any suitable manner including, for example, laser cutting.

Figure 10A:
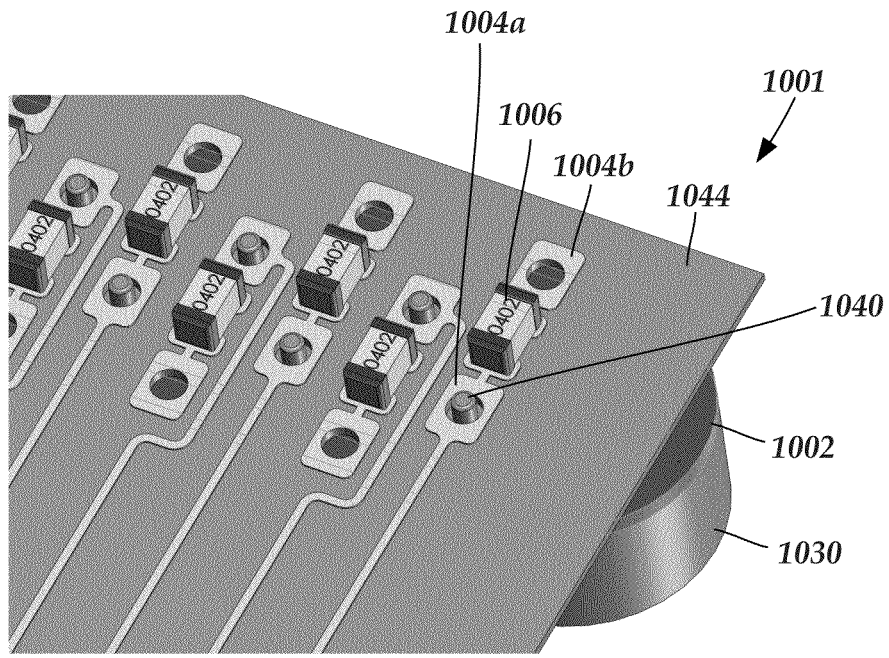
FIG. 10A is a schematic top perspective view of another embodiment of a RF-diverting assembly coupled to a flex circuit and to a feedthrough housing, according to the invention.

Turning to FIG. 10A, in at least some embodiments the conductive pads and the capacitors are disposed directly on the flex circuit. In at least some embodiments, the conductive pads and the capacitors are disposed on a first major surface of the flex circuit and the feedthrough ground is disposed on an opposing second major surface of the flex circuit. In other words, in at least some embodiments the flex circuit is sandwiched between the conductive pads/capacitive elements and the feedthrough ground.

Figure 10B:
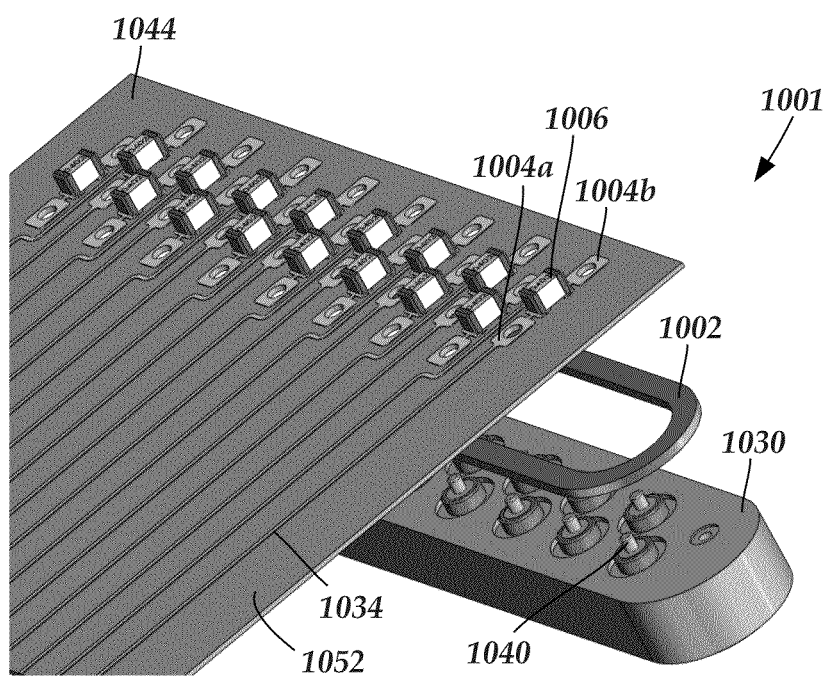
FIG. 10B is a schematic top perspective exploded view of one embodiment of the RF-diverting assembly of FIG. 10A, the flex circuit of FIG. 10A, and the feedthrough housing of FIG. 10A to which the RF-diverting assembly couple, according to the invention.

FIG. 10A is a schematic top perspective view of one embodiment of the flex circuit 1044, a RF-diverting assembly 1001, and the feedthrough housing 1030. FIG. 10B is a schematic top perspective exploded view of one embodiment of the flex circuit 1044, the RF-diverting assembly 1001, and the feedthrough housing 1030. A plurality of conductive pathways, such as conductive pathway 1034, are disposed on the flex circuit 1044. A plurality of feedthrough pins, such as feedthrough pin 1040, extend from the feedthrough housing 1030.

The RF-diverting assembly 1001 includes a plurality of capacitive elements, such as capacitive element 1006; a plurality of first contact regions, such as first contact region 1004a; a plurality of second contact regions, such as second contact region 1004b; and a feedthrough ground 1002. In FIGS. 10A-10B, the first contact regions 1004a, the second contact regions 1004b, and the capacitive elements 1006 are each coupled directly to a first major surface 1052 of the flex circuit 1044.

The first contact regions 1004a, the second contact regions 1004b, and the capacitive elements 1006 are configured such that the capacitive elements 1006 each electrically couple one of the first contact regions 1004a to a different one of the second contact regions 1004b. The first contact regions 1004a are each configured to electrically couple (e.g., welding, soldering, conductive adhesive, or the like) to one of the feedthrough pins 1040 (and also to one of the conductive pathways 1034. The second contact regions 1004b are each configured and arranged to electrically couple (e.g., welding, conductive adhesive, or the like) with the feedthrough ground 1002 which, in turn, is coupleable to the feedthrough housing 1030. The contact regions 1004a and 1004b can be formed on the flex circuit 1044 using standard circuit-forming techniques (e.g., photolithography, or the like). In at least some embodiments, the first contact regions 1004a and the second contact regions 1004a are formed as conductive pads.

In FIGS. 10A-10B, the first contact regions 1004a each define an aperture extending through the flex circuit 1044 for coupling the first contact regions 1004a (disposed on the first major surface 1052 of the flex circuit 1044) with the feedthrough pins 1040 (which extend through the flex circuit 1044 from an opposing second major surface of the flex circuit 1044). In FIGS. 10A-10B, the second contact regions 1004b each define an aperture extending through the flex circuit 1044 for coupling the second contact regions 1004b (disposed on the first major surface 1052 of the flex circuit 1044) with the feedthrough ground 1002 (which is coupled to the opposing second major surface of the flex circuit 1044).

The capacitive elements 1006, the first contact regions 1004a, and the second contact regions 1004b can be coupled to the flex circuit 1044 in any suitable manner including, for example, soldering, conductive adhesive, or the like. The feedthrough ground 1002 can be coupled to the feedthrough housing 1030 in any suitable manner including, for example, welding, brazing, or the like. The feedthrough ground 1002 can be coupled to the flex circuit 1044 in any suitable manner including, for example, welding, brazing, conductive adhesive, or the like. The feedthrough ground 1002 can be coupled to the flex circuit 1044 after the feedthrough ground 1002 is coupled to the feedthrough housing 1030.

In at least some embodiments, the feedthrough housing 1020 is formed from a material (e.g., titanium, or the like) that cannot be soldered directly to the flex circuit 1044. In at least some embodiments, the feedthrough ground 1002 is sputtered onto the feedthrough housing 1030 using any suitable metallic material including, for example, gold, silver, palladium, nickel, or the like. In which case, the sputtered feedthrough ground 1002 may be soldered directly to the flex circuit 1044.

Figure 11A:
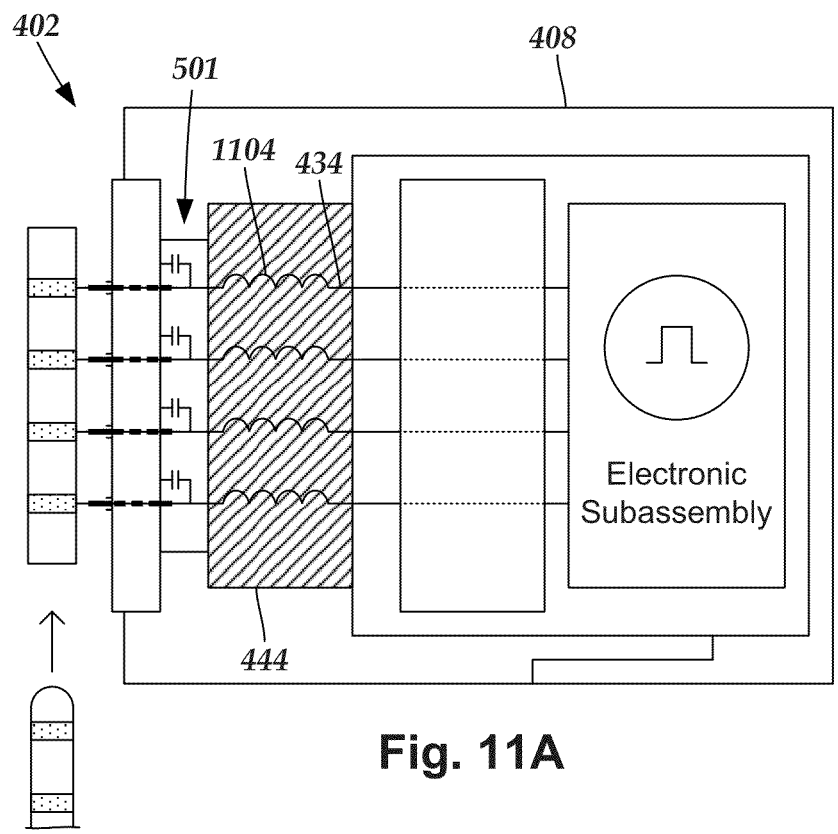
FIG. 11A is a schematic top view of another embodiment of the control module of FIG. 4A, the control module including a plurality of inductors disposed on conductive pathways extending within the control module between a feedthrough housing and an electronic subassembly, according to the invention.
Figure 11B:
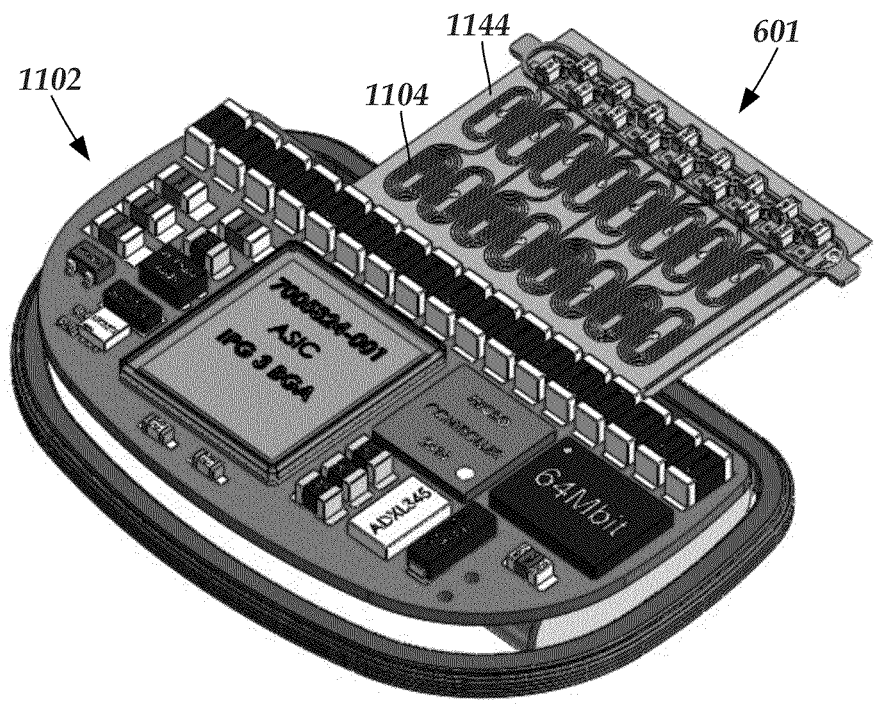
FIG. 11B is a schematic top perspective view of one embodiment of the inductors of FIG. 11A disposed in another embodiment of a control module, according to the invention.

Turning to FIG. 11A-11B, in at least some embodiments the RF-diverting assembly includes a plurality of inductors. Since the operational frequencies of the electrical stimulation system are much lower than the operational frequencies of a typical MRI system, inductors can be selected to block the flow of induced current at the comparatively-high frequencies of the MRI, while causing little or no effect to the comparatively-low operational frequencies of the electrical stimulation system.

FIG. 11A is a schematic diagram of another embodiment of the control module 402. A plurality of inductors, such as inductor 1104, are disposed along the conductive pathways 434. The inductors 1104 may be disposed at any suitable location along a length of the conductive pathways 434. In FIG. 11A, the inductors 1104 are shown disposed along the flex circuit 444. The inductors 1104 can be formed in any suitable manner including, for example, etching one or more inductors 1104 into the flex circuit 444, or attaching one or more inductors onto the flex circuit 444.

FIG. 11B is a schematic top perspective view of one embodiment of the RF-diverting assembly 601 coupled to a flex circuit 1144 of a control module 1102. In FIG. 11B, the RF-diverting assembly 601 includes a plurality of inductive elements, such as inductor 1104 disposed on the flex circuit 1144. In FIG. 11B, the inductors 1104 are shown as a plurality of loops. In at least some embodiments, one or more of the conductive pads 604 are coupled directly to one or more of the inductive elements 1104.

The above-described embodiments of the RF-diverting assembly are easy to manufacture, as compared to conventional filters. The above-described embodiments of the RF-diverting assembly are inexpensive to manufacture, as compared to conventional filters. Additionally, the above-described embodiments of the current-dispersing element have volumetric profiles that are significantly smaller than other conventional filters.

Figure 12:
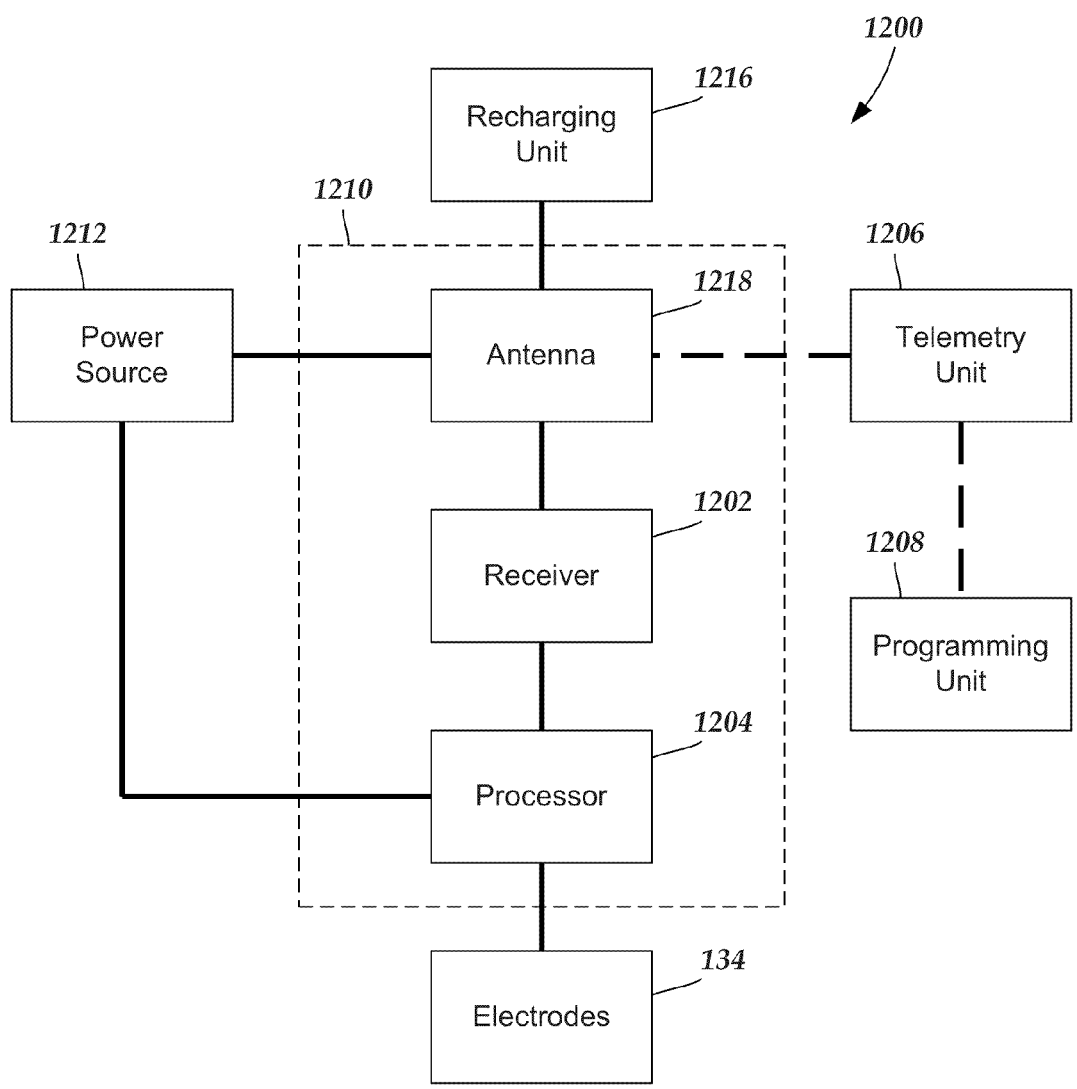
FIG. 12 is a schematic overview of one embodiment of components of an electrical stimulation system, according to the invention.

FIG. 12 is a schematic overview of one embodiment of components of an electrical stimulation system 1200 including an electronic subassembly 1210 disposed within a control module. It will be understood that the electrical stimulation system can include more, fewer, or different components and can have a variety of different configurations including those configurations disclosed in the stimulator references cited herein.

Some of the components (for example, power source 1212, antenna 1218, receiver 1202, and processor 1204) of the electrical stimulation system can be positioned on one or more circuit boards or similar carriers within a sealed housing of an implantable pulse generator, if desired. Any power source 1212 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 1218 or a secondary antenna. The external power source can be in a device that is mounted on the skin of the user or in a unit that is provided near the user on a permanent or periodic basis.

If the power source 1212 is a rechargeable battery, the battery may be recharged using the optional antenna 1218, if desired. Power can be provided to the battery for recharging by inductively coupling the battery through the antenna to a recharging unit 1216 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1204 is generally included to control the timing and electrical characteristics of the electrical stimulation system. For example, the processor 1204 can, if desired, control one or more of the timing, frequency, strength, duration, and waveform of the pulses. In addition, the processor 1204 can select which electrodes can be used to provide stimulation, if desired. In some embodiments, the processor 1204 may select which electrode(s) are cathodes and which electrode(s) are anodes. In some embodiments, the processor 1204 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1208 that, for example, allows modification of pulse characteristics. In the illustrated embodiment, the processor 1204 is coupled to a receiver 1202 which, in turn, is coupled to the optional antenna 1218. This allows the processor 1204 to receive instructions from an external source to, for example, direct the pulse characteristics and the selection of electrodes, if desired.

In one embodiment, the antenna 1218 is capable of receiving signals (e.g., RF signals) from an external telemetry unit 1206 which is programmed by a programming unit 1208. The programming unit 1208 can be external to, or part of, the telemetry unit 1206. The telemetry unit 1206 can be a device that is worn on the skin of the user or can be carried by the user and can have a form similar to a pager, cellular phone, or remote control, if desired. As another alternative, the telemetry unit 1206 may not be worn or carried by the user but may only be available at a home station or at a clinician's office. The programming unit 1208 can be any unit that can provide information to the telemetry unit 1206 for transmission to the electrical stimulation system 1200. The programming unit 1208 can be part of the telemetry unit 1206 or can provide signals or information to the telemetry unit 1206 via a wireless or wired connection. One example of a suitable programming unit is a computer operated by the user or clinician to send signals to the telemetry unit 1206.

The signals sent to the processor 1204 via the antenna 1218 and receiver 1202 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1200 to cease operation, to start operation, to start charging the battery, or to stop charging the battery. In other embodiments, the stimulation system does not include an antenna 1218 or receiver 1202 and the processor 1204 operates as programmed.

Optionally, the electrical stimulation system 1200 may include a transmitter (not shown) coupled to the processor 1204 and the antenna 1218 for transmitting signals back to the telemetry unit 1206 or another unit capable of receiving the signals. For example, the electrical stimulation system 1200 may transmit signals indicating whether the electrical stimulation system 1200 is operating properly or not or indicating when the battery needs to be charged or the level of charge remaining in the battery. The processor 1204 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A method of forming a control module for an electrical stimulation system, the control module comprising an electronic subassembly disposed in an inner space of a casing and a feedthrough housing disposed along a portion of the casing, the method comprising:
    forming, an RF-diverting assembly, the RF-diverting assembly comprising a plurality of capacitive elements electrically coupled to a feedthrough ground;
    electrically coupling the plurality of capacitive elements to a plurality of conductive pathways extending along a first major surface of a non-conductive substrate, wherein the plurality of capacitive elements are disposed on the first major surface of the non-conductive substrate;
    electrically coupling the plurality of conductive pathways to a plurality of feedthrough pins extending through the feedthrough housing from a location external to the casing to a location within the inner space of the casing;
    electrically coupling the plurality of conductive pathways to the electronic subassembly such that the plurality of conductive pathways electrically couple the plurality of feedthrough pins to the electronic subassembly;
    electrically coupling the feedthrough ground to at least one electrically-conductive portion of the feedthrough housing wherein the feedthrough ground is disposed on a second major surface, opposite the first major surface, of the non-conductive substrate; and
    electrically coupling the at least one electrically-conductive portion of the feedthrough housing to at least one electrically-conductive portion of an outer surface of the casing.

2. The method of claim 1, wherein electrically coupling the plurality of capacitive elements to a plurality of conductive pathways disposed along a non-conductive substrate comprises electrically coupling the plurality of capacitive elements to a plurality of conductive pathways via a plurality of conductive pads of the RF-diverting assembly.

3. The method of claim 2, wherein electrically coupling the plurality of capacitive elements to a plurality of conductive pathways via a plurality of conductive pads of the RF-diverting assembly comprises mechanically coupling each of the plurality of conductive pads directly to the non-conductive substrate.

4. The method of claim 2, wherein electrically coupling the plurality of capacitive elements to a plurality of conductive pathways via a plurality of conductive pads of the RF-diverting assembly comprises electrically coupling each of the plurality of conductive pads to a different one of the plurality of conductive pathways extending along the non-conductive substrate.

5. The method of claim 2, wherein electrically coupling the plurality of capacitive elements to a plurality of conductive pathways via a plurality of conductive pads of the RF-diverting assembly comprises removably attaching the plurality of conductive pads to the non-conductive substrate.

6. The method of claim 1, wherein the feedthrough housing is formed from titanium.

7. The method of claim 1, wherein electrically coupling the plurality of capacitive elements to a plurality of conductive pathways extending along a non-conductive substrate comprises electrically coupling the plurality of capacitive elements to a plurality of conductive pathways extending along a flex circuit.

8. The method of claim 1, wherein electrically coupling the feedthrough ground to at least one electrically-conductive portion of the feedthrough housing comprises electrically coupling the feedthrough ground formed from at least one of nickel or nickel alloy to at least one electrically-conductive portion of the feedthrough housing.

9. The method of claim 1, wherein electrically coupling the feedthrough ground to at least one electrically-conductive portion of the feedthrough housing comprises mechanically coupling the feedthrough ground directly to the at least one electrically-conductive portion of the feedthrough housing.

10. The method of claim 1, wherein electrically coupling the feedthrough ground to at least one electrically-conductive portion of the feedthrough housing comprises mechanically coupling the feedthrough ground to the at least one electrically-conductive portion of the feedthrough housing via one or more coupling pads disposed along the feedthrough ground.

11. The method of claim 1, wherein electrically coupling the feedthrough ground to at least one electrically-conductive portion of the feedthrough housing comprises at least one of welding or brazing the feedthrough ground to the electrically conductive portion of the feedthrough housing.

12. The method of claim 1, wherein electrically coupling the feedthrough ground to at least one electrically-conductive portion of the feedthrough housing comprises depositing the feedthrough ground onto the electrically-conductive portion of the feedthrough housing.

13. The method of claim 1, further comprising mechanically coupling the feedthrough ground to the non-conductive substrate.

14. The method of claim 13, wherein mechanically coupling the feedthrough ground to the non-conductive substrate comprises mechanically coupling the feedthrough ground to the non-conductive substrate such that the non-conductive substrate is sandwiched between the feedthrough ground and the feedthrough housing.

15. The method of claim 1, further comprising disposing a connector configured and arranged for receiving a lead or lead extension external to the casing and in proximity to the feedthrough housing.

16. The method of claim 15, wherein disposing a connector configured and arranged for receiving a lead or lead extension external to the casing and in proximity to the feedthrough housing comprises electrically coupling first ends of the plurality of feedthrough pins to connector contacts disposed in the connector.

17. The method of claim 1, further comprising electrically coupling each of a plurality of inductors to a different one of the plurality of conductive pathways.

18. The method of claim 1, further comprising coupling together adjacent capacitive elements of the plurality of capacitive elements with adhesive.

19. The method of claim 1, further comprising electrically coupling the electronic subassembly to the at least one electrically-conductive portion of the casing via a ground line.

* * * * *